United States Patent
Iino et al.

(10) Patent No.: US 6,794,378 B2
(45) Date of Patent: Sep. 21, 2004

(54) HETEROCYCLIC COMPOUNDS AND MEDICAL USE THEREOF

(75) Inventors: Yukio Iino, Kawasaki (JP); Koichi Fujita, Kawasaki (JP); Ariko Kodaira, Kawasaki (JP); Toshihiro Hatanaka, Kawasaki (JP); Kenji Takehana, Kawasaki (JP); Tsuyoshi Kobayashi, Kawasaki (JP); Atsushi Konishi, Kawasaki (JP); Takashi Yamamoto, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/029,871

(22) Filed: Dec. 31, 2001

(65) Prior Publication Data

US 2002/0133005 A1 Sep. 19, 2002

Related U.S. Application Data

(63) Continuation of application No. PCT/JP00/04298, filed on Jun. 29, 2000.

(30) Foreign Application Priority Data

Jul. 1, 1999 (JP) ............................................. 11-187959
Mar. 15, 2000 (JP) ....................................... 2000-071706

(51) Int. Cl.⁷ ...................... A61K 31/33; A61K 31/505; A61K 31/44; C07D 239/02; C07D 213/00
(52) U.S. Cl. .................. 514/183; 514/252.01; 514/253; 514/275; 514/277; 514/345; 514/352; 514/351; 514/247; 544/224; 544/239; 544/315; 544/330; 546/1; 546/290; 546/304
(58) Field of Search ................................ 514/183, 247, 514/252.01, 253, 275, 277, 345, 352, 351; 544/224, 239, 315, 330; 546/1, 290, 304

(56) References Cited

U.S. PATENT DOCUMENTS 6,563,002 B2 5/2003 Iino et al.

FOREIGN PATENT DOCUMENTS

| EP | 102476 | * | 3/1984 |
|---|---|---|---|
| WO | 9313739 | * | 7/1993 |
| WO | WO 97/17958 A1 | | 5/1997 |
| WO | WO 97/24343 A1 | | 7/1997 |
| WO | 99/15164 | | 4/1999 |
| WO | 99/61019 | | 12/1999 |
| WO | WO 00/15603 A1 | | 3/2000 |
| WO | 2001094353 | * | 12/2001 |

OTHER PUBLICATIONS

Chemical Abstract DN 120:107751, also cited as WO 9313739.*
Chemical Abstract DN 136:37500–2001:904182, also cited as WO 2001094353 dated 20011213.*
Chemical Abstr. 120:107751–1994:107751, also cited as WO 9313739 dated 19930722.*
Chical Abstract DN 136:37500.2001:904182, also cited as WO 2001094353 dated 20011213.*
XP–002201911 (Abstract only).

* cited by examiner

Primary Examiner—Richard L. Raymond
Assistant Examiner—Sudhaker B. Patel
(74) Attorney, Agent, or Firm—Oblon, Spivak, McClelland, Maier & Neustadt, P.C.

(57) ABSTRACT

The present invention provides an AP-1 activation inhibitor, a NF-kappaB activation inhibitor, an inflammatory cytokine production inhibitor, a production inhibitor for matrix metalloprotease or an inflammatory cell adhesion factor expression inhibitor, which contains a heterocyclic compound or a pharmaceutically acceptable salt thereof as an active ingredient.

32 Claims, No Drawings

HETEROCYCLIC COMPOUNDS AND MEDICAL USE THEREOF

This application is a continuation of International Patent Application PCT/JP00/04298, which was filed on Jun. 29, 2000, and which claims priority to Japanese Patent Application 11-187959, which was filed on Jul. 1, 1999, and to Japanese Patent Application 2000-71706, which was filed on Mar. 15, 2000, all of which are incorporated herein by reference.

BACKGROUND OF THE INVENTION

The present invention relates to a therapeutic agent for various kinds of inflammatory disease.

It is known that various inflammatory diseases, rheumatoid diseases, immunoreactive diseases, cancer metastasis and viral diseases are caused by the abnormal production of inflammatory cytokines and matrix metalloprotease and also by the increase in the expression of inflammatory cell adhesion molecules.

Although various medicines for these diseases were developed in the prior art, further development of a medicine having a stronger efficiency, higher safety and weaker side effects is demanded.

The pathophysiological states of various chronic inflammatory diseases are considered to be caused by the continuous production of inflammation mediators such as cytokines particularly, inflammatory cytokines including IL-1, IL-2, IL-6, IL-8 and tumor necrosis factor (TNF)], adhesion molecules, tissue destroying enzymes (such as matrix metalloprotease), etc. by the continuous extracellular stimulation.

The inflammatory mediators are produced because the gene expression is activated by the extracellular stimulation. A substance having the most important role in this step is a transcription factor known as AP-1 or NF-kappa B. Namely, it is expected that when the activation of AP-1/NF-kappa B can be inhibited, the development of inflammation and the advance thereof into chronic stage can be prevented and that such a method will be a hopeful treatment of inflammatory diseases such as rheumatoid arthritis and various autoimmune diseases.

Glucocorticoid hormone (GC) which strongly inhibits the activation of intracellular AP-1 and NF-kappa B has been used as a powerful anti-inflammatory agent and immunosuppressant. However, the use of GC as a medicine is limited because it has various side effects due to hormonic action thereof and it causes rebound phenomenon.

DISCLOSURE OF THE INVENTION

An object of the present invention is to provide a new compound effective to cure chronic inflammatory disease with high activity and fewer side effects.

Another object of the present invention is to provide a pharmaceutical composition comprising corresponding new compound.

After intensive investigations made for the purpose of finding compounds having a strong activity of inhibiting the activation of AP-1 and NF-kappa B and useful as a strong remedy for chronic inflammatory diseases, the inventors have found that compounds of general formula (I) which will be described below have this effect. The present invention has been completed on the basis of this finding.

That is, the present invention provides a heterocyclic compound represented by the following general formula (I) or a pharmaceutically acceptable salt thereof.

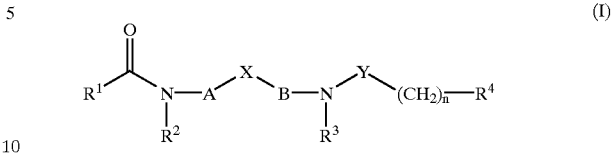

wherein $R^1$ is a cycloalkyl group, a cycloalkyl group having a substituent(s), a cycloalkenyl group or a cycloalkenyl group having a substituent(s); each $R^2$ and $R^3$ is a hydrogen atom or an alkyl group; $R^4$ is an alkyl group, an alkyl group having a substituent(s), an alkenyl group, an alkenyl group having a substituent(s), a cycloalkyl group, a cycloalkyl group having a substituent(s), a cycloalkenyl group, a cycloalkenyl group having a substituent(s), an aryl group, an aryl group having a substituent(s), an aromatic heterocyclic group having at least one hetero-atom within a ring or an aromatic heterocyclic group having a substituent(s) and at least one hetero-atom within a ring; A is a heterocyclic ring or a heterocyclic ring having a substituent(s); B is an aromatic ring, an aromatic ring having a substituent(s), a heterocyclic ring or a heterocyclic ring having a substituent (s); n is an integer selected from 0 to 6; —Y— is an interatomic bond, —CO—, —CO—O—, —CO—$NR^5$—, —CS—$NR^6$—, —SO—, —$SO_2$— wherein each $R_5$ and $R_6$ is a hydrogen atom or an alkyl group; and —X— is an interatomic bond, —O—, —O—$CHR^7$—, —$CHR^8$—O—, —O—CO—, —CO—O—, —O—CS—, —CS—O—, —S—, —SO—, —$SO_2$—, —S—$CHR^9$—, —$CHR^{10}$—S—, —S—CO—, —CO—S—, —S—CS—, —CS—S—, —$SO_2$—$NR^{11}$—, —$NR^{12}$—$SO_2$—, —$NR^{13}$—, —$NR^{14}$—$CHR^{15}$—, —$CHR^{16}$—$NR^{17}$—, —CO—, —C(=$NOR^{18}$)—, —C(=$CHR^{19}$)—, —CO—$CHR^{20}$—, —$CHR^{21}$—CO—, —CO—$NR^{22}$—, —$NR^{23}$—CO—, —$CR^{24}R^{25}$—, —$CHR^{26}$—$CHR^{27}$—, —$CR^{28}$=$CR^{29}$—, —O—$CHR^{30}$—$CHR^{31}$— wherein each $R^7$, $R^8$, $R^9$, $R^{10}$, $R^{15}$, $R^{16}$, $R^{20}$, $R^{21}$, $R^{24}$, $R^{28}$, $R^{29}$, $R^{30}$ and $R^{31}$ is either of a hydrogen atom or an alkyl group; each of $R^{11}$, $R^{12}$, $R^{13}$, $R^{14}$, $R^{17}$, $R^{18}$, $R^{19}$, $R^{22}$ and $R^{23}$ is either of a hydrogen atom, an alkyl group or an acyl group; each of $R^{26}$ and $R^{27}$ is either of a hydrogen atom, a hydroxy group or an alkyl group; and $R^{25}$ is a hydrogen atom, a hydroxy group, an alkyl group, an alkyl group having a substituent(s), a mercapto group, an alkoxy group, an alkylthio group, an acyloxy group, an amino group, an alkylamino group, an amino group substituted with an amino protective group, a carboxyl group, an alkoxycarbonyl group, an aminocarbonyl group, or a cyano group.

Further, the present invention provides an AP-1 or NF-kappaB activation inhibitor, an inflammatory cytokine production inhibitor, a matrix-metalloprotease production inhibitor and an inflammatory cell adhesion factor expression inhibitor, each of which comprises, as an active ingredient, the above-described heterocyclic compound or a pharmaceutically acceptable salt thereof, and these can be used as an anti-inflammatory agent, an anti-rheumatism agent, an immuno-suppressive agent, a cancer metastasis inhibitor, an antiviral agent or a curative agent for arterial sclerosis.

It is to be noted that a heterocyclic compound or a pharmaceutically acceptable salt thereof according to the present invention, in which $R^1$ is a cycloalkyl group having a substituent(s), may be more effective. Among these, compounds wherein $R^1$ is a cyclopropyl group having a substituent(s), more specifically either of a 2,2- dimethylcyclopropyl group or a 2,2-dichlorocyclopropyl group are of high activity. Among these, higher activity can be obtained by compounds wherein $R^4$ is 2,2-dimethylcyclopropyl group or 2,2-dichlorocyclopropyl group, —Y— is —CO— and n=0; or compounds wherein $R^4$ is an aryl group or an aryl group having a substituent(s), —Y— is —CO— and n=1; or compounds wherein $R^4$ is an aryl group or an aryl group having a substituent(s), —Y— is an interatomic bond and n is 1 or 2.

BEST MODE FOR CARRYING OUT THE PRESENT INVENTION

Examples of the halogen atom in the present invention include a fluorine atom, a chlorine atom, a bromine atom and an iodine atom.

The alkyl group means a straight-chain or branched-chain alkyl group having 1 to 6 carbon atoms such as a methyl group, an ethyl group, a n-propyl group, an isopropyl group, a n-butyl group, an isobutyl group, a sec-butyl group, a tert-butyl group, a n-pentyl group, an isopentyl group, a tert-pentyl group, a neopentyl group, a 2-pentyl group, a 3-pentyl group, a n-hexyl group and a 2-hexyl group, wherein the methyl group and the ethyl group are preferable.

The alkenyl group means a straight-chain or branched-chain alkenyl group having 1 to 6 carbon atoms such as a 1-propenyl group, an allyl group, an isopropenyl group, a 1-butenyl group and a 2-butenyl group.

The cycloalkyl group means a cyclic alkyl group having 3 to 6 carbon atoms such as a cyclopropyl group, a cyclobutyl group, a cyclopentyl group and a cyclohexyl group, wherein the cyclopropyl group is a preferable cycloalkyl group.

The cycloalkenyl group means a cyclic alkenyl group having 3 to 6 carbon atoms such as a cyclopropenyl group, a cyclobutenyl group, a cyclopentenyl group and a cyclohexenyl group.

The hetero atom means specifically, for example, an oxygen atom, a sulfur atom and a nitrogen atom, wherein nitrogen atom is preferable.

The an aryl group means specifically, for example, a phenyl group, an indenyl group, a naphthyl group and a fluorenyl group, wherein phenyl group is preferable.

The aromatic heterocyclic group having at least one hetero atom means specifically, for example, a pyranyl group, a pyridyl group, a pyridazyl group, a pyrimidyl group, a pyrazyl group, a furyl group, a thienyl group, a pyrrolyl group, an oxazolyl group, an isoxazolyl group, a thiazolyl group, an isothiazolyl group, an imidazolyl group, a triazolyl group, a tertazolyl group, a pyrazolyl group, a furazanyl group, a thiadiazolyl group and a indolyl group, wherein pyridyl group, pyrimidyl group, imidazolyl group and triazolyl group are preferable, and among them pyridyl group is more preferable.

The acyl group means a formyl group, an acyl group having a straight-chain, a branched-chain or a cyclic alkyl group having 1 to 6 carbon atoms or an acyl group having a substituted or unsubstituted aryl group, and specifically, it includes, for example, a formyl group, an acetyl group, a propionyl group, a butyloyl group, an isobutyloyl group, a valeloyl group, an isovaleloyl group, a pivaloyl group, a hexanoyl group, an acryloyl group, a metacryloyl group, a crotonoyl group, an isocrotonoyl group, a benzoyl group and a naphthoyl group.

The acyloxy group means a formyloxy group or an acyloxy group having a straight-chain, a branched chain or a cyclic alkyl group having 1 to 6 carbon atoms or an acyloxy group having an substituted or unsubstituted aryl group, and specifically, it includes, for example, a formyloxy group, an acetoxy group, a propionyloxy group, a butyloyloxy group, an isobutyloyloxy group, a valeloyloxy group, an isovaleloyloxy group, a pivaloyloxy group, a hexanoyloxy group, an acryloyloxy group, a metacryloyloxy group, a crotonoyloxy group, an isocrotonoyloxy group, a benzoyloxy group and a naphthoyloxy group.

The alkoxy group means an alkoxy group having a straight chain, a branched chain or a ring alkyl group having 1 to 6 carbon atoms such as a methoxy group, an ethoxy group, a n-propoxy group, an isopropoxy group, a n-butoxy group, an isobutoxy group, a sec-butoxy group, a tert-butoxy group, a cyclopropyloxy group, a cyclobutoxy group, a cyclopentyloxy group and a cyclohexyloxy group, wherein methoxy group and ethoxy group are preferable.

The alkylthio group means an alkylthio group having a straight-chain, a branched-chain or a ring alkyl group having 1 to 6 carbon atoms such as a methylthio group, an ethylthio group, a n-propylthio group, an isopropylthio group, a n-butylthio group, a isobutylthio group, a sec-butylthio group, a tert-butylthio group, a cyclopropylthio group, a cyclobutylthio group, a cyclopentylthio group and a cyclobutylthio group.

The alkylamino group means an amino group mono-substituted or bi-substituted with alkyl group, the alkyl group including those having been specified in above description of the "alkyl group". Specifically, the alkylamino group includes, for example, an amino group, a methylamino group, an ethylamino group, a propylamino group, an isopropylamino group, a dimethylamino group, a diethylamino group, a dipropylamino group, a diisopropylamino group and a methylethylamino group.

The amino protective group means a normally used protective group, including unlimitedly those substances that can protect the amino group against various reactions. Specifically, the amino protective group includes an acyl group such as a formyl group, an acetyl group and a pivaloyl group; and an alkoxycarbonyl group such as a methoxycarbonyl group, an ethoxycarbonyl group, a tert-butoxycarbonyl group and a (fluorene-9-yl) methoxycarbonyl group.

The alkoxycarbonyl group includes specifically, for example, methoxycarbonyl group, ethoxycarbonyl group, a propoxycarbonyl group, an isopropoxycarbonyl group, a n-butoxycarbonyl group, an isobutoxycarbonyl group, a sec-butoxycarbonyl group and a tert-butoxycarbonyl group.

In the description of $R^1$, the term "having a substituent(s)" in the expressions "a cycloalkyl group having a substituent (s)", "a cycloalkenyl group having a substituent(s)" and "a cyclopropyl group having a substituent(s)" means being substituted with at least one or more substituents, wherein the substituents may be the same or different and a position of the substituent(s) is not specifically limited but may be arbitrarily determined. Specifically, the term includes, for example, a halogen atom, an alkyl group, a substituted alkyl group, a carboxyl group, an alkoxycarbonyl group, a cyano group, an alkylamino group, and an amino group substituted with an amino protective group.

In the description of $R^4$, the term "having a substituent(s)" in the expression "an alkyl group having a substituent(s)" means being substituted with at least one or more substituents, wherein the substituents may be the same or different and a position of the substituent(s) is not specifically limited but may be arbitrarily determined. Specifically, the term includes, for example, a halogen atom, a hydroxy group, an alkoxy group, a carboxyl group, an alkoxycarbonyl group, a cyano group, an alkylamino group, and an amino group substituted with an amino protective group.

In the description of $R^4$, the term "having a substituent(s)" in the expressions "a cycloalkyl group having a substituent(s)" and "a cycloalkenyl group having a substituent(s)" means being substituted with at least one or more substituents, wherein the substituents may be the same or different and a position of the substituent(s) is not specifically limited but may be arbitrarily determined. Specifically, the term includes, for example, a halogen atom, a hydroxy group, an alkoxy group, a carboxyl group, an alkoxycarbonyl group, a cyano group, an alkylamino group, and an amino group substituted with an amino protective group.

In the description of $R^4$, the term "having a substituent(s)" in the expressions "an aryl group having a substituent(s)" and "an aromatic heterocyclic group having one or more hetero atoms having a substituent(s)" means having one to three substituents on the ring, wherein the substituents may be the same or different and a position of the substituent(s) is not specifically limited but may be arbitrarily determined. Specifically, the term includes, for example, a halogen atom, an alkyl group, a substituted alkyl group, a hydroxy group, an alkoxy group, a carboxyl group, an alkoxycarbonyl group, a cyano group, an alkylamino group, and an amino group substituted with an amino protective group.

The term "heterocyclic ring" in the expression "a heterocyclic ring or a heterocyclic ring having a substituent(s)" in the description with reference to A and in "a heterocyclic ring or a heterocyclic ring having a substituent(s)" in the description with reference to B is used to mean a heterocyclic ring comprising a single ring or two rings with 5 to 7 members consisting of carbon and nitrogen, oxygen, sulfur and so on, and includes specifically, for example, pyridine, dihydropyran, pyridazine, pyrimidine, pyrazine, triazine, tetrazine, pyrrole, furan, thiophene, oxazole, isoxazole, thiazole, isothiazole, imidazole, triazole, pyrazole, furazan, thiadiazole, pyrrolidine, piperidine, piperazine, indole, benzopyrazole, benzoxazole, benzothiazole, benzoimidazole, benzofuran, benzothiophene, pyrazolopyridine, quinoline, isoquinoline, naphthylidine and benzodiazepine. Preferably, the heterocyclic ring should be the one shown in the following diagram, and more preferably pyridine. It is to be noted that for those bonds in both sides with respect to A and B, i.e., the bonds of $NR^2$ and X with A and the bonds X and $NR^3$ with B, the bond positions of them are not limited but may be arbitrarily determined.

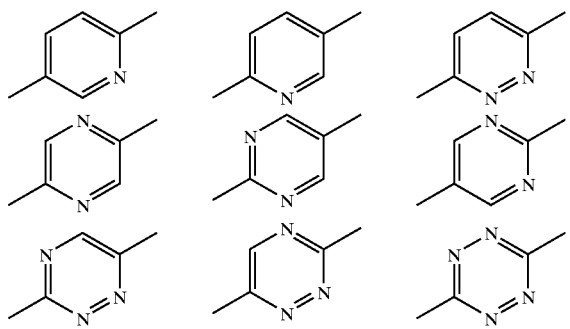

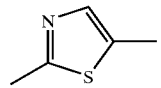

In the above formulas, the first two formulas are preferred.

The term "aromatic heterocyclic ring" in the expresion "an aromatic heterocyclic ring or an aromatic heterocyclic ring having a substituent(s)" in the description with reference to A and "an aromatic heterocyclic ring or an aromatic heterocyclic ring having a substituent(s)" in the description with reference to B represents an unsaturated aromatic heterocyclic ring comprising a single ring or two rings with 5 to 7 members consisting of carbon and nitrogen, oxygen, sulfur and so on, and includes specifically, for example, pyridine, dihydropyran, pyridazine, pyrimidine, pyrazine, triazine, tetrazine, pyrrole, furan, thiophene, oxazole, isoxazole, thiazole, isothiazole, imidazole, triazole, pyrazole, furazan, thiadiazole, indole, benzopyrazole, benzoxazole, benzothiazole, benzoimidazole, benzofuran, benzothiophene, pyrazolopyridine, quinoline, isoquinoline, naphthylidyne and benzodiazepine.

The term "an aromatic ring" in the expression "an aromatic ring or an aromatic ring having a substituent(s)" in the description with reference to B represents an aromatic ring comprising a single ring or two rings consisting of carbon atoms, and includes specifically, for example, benzene, naphthalene, indene and naphthalene, wherein benzene is preferable. It is to be noted that the positions of the bonds at both sides with respect to B, i.e., the bonds with X and $NR^3$, are not specifically limited but may be arbitrary determined.

The term "having a substituent(s)" in the expression "a heterocyclic ring having a substituent(s)" in the description with reference to A and "an aromatic ring having a substituent(s)" in the description with reference to B means having one to three substituents on the ring, wherein the substituents may be the same or different and the position of the substituent(s) is not specifically limited but may be arbitrarily determined. Specifically, the term includes, for example, a halogen atom, an alkyl group, a substituted alkyl group, a hydroxy group, an alkoxy group, a carboxyl group, an alkoxycarbonyl group, a cyano group, an alkylamino group or an amino group substituted with an amino protective group.

As heterocyclic compounds represented by the general formula (I) in claim 1 and pharmaceutically acceptable salts thereof, the preferred are those wherein B is a phenylene group; $R^1$ is a cycloalkyl group having a substituent(s) or a cycloalkenyl group having a substituent(s); $R^2$ is a hydrogen atom or an alkyl group; $R^3$ is a hydrogen atom or an alkyl group; $R^4$ is an alkyl group which may be substituted, a cycloalkyl group which may be substituted, a cycloalkenyl group which may be substituted, an aryl group which may be substituted or an aromatic heterocyclic ring group which may be substituted and also has one or more hetero atoms; —X— is —O—, —O—CHR$^7$—, —CHR$^8$—O—, —O—CO—, —CO—O—, —O—CS—, —CS—O—, —S—, —SO—, —SO$_2$—, —S—CHR$^9$—, —CHR$^{10}$—S—, —S—CO—, —CO—S—, —S—CS—, —CS—S—, —SO$_2$—NR$^{11}$—, —NR$^{12}$—SO$_2$—, —NR$^{13}$—, —NR$^{14}$—CHR$^{15}$—, —CHR$^{16}$—NR$^{17}$—, —CO—, —C(=NOR$^{18}$)—, —C(=CNR$^{19}$)—, —CO—CHR$^{20}$—, —CHR$^{21}$—CO—, —CO—NR$^{22}$—, —NR$^{23}$—CO—, —CR$^{24}$R$^{25}$—, —CHR$^{26}$—CHR$^{27}$— or —CR$^{28}$=CR$^{29}$— wherein $R^7$, $R^8$, $R^9$, $R^{10}$, $R^{20}$, $R^{21}$, $R^{24}$, $R^{28}$ and $R^{29}$ are either of a hydrogen atom or an alkyl group; $R^{11}$, $R^{12}$, $R^{13}$, $R^{14}$, $R^{17}$, $R^{18}$, $R^9$, $R^{22}$ and $R^{23}$ are either of a hydrogen atom, an alkyl group or an acyl group; $R^{15}$ and $R^{16}$ are a hydrogen atom or an alkyl group; $R^{26}$ and $R^{27}$ are either of a hydrogen atom, a hydroxy group or an alkyl group; $R^{25}$ is a hydrogen atom, an hydroxy group, an alkyl group which may be substituted, a mercapto group, an alkoxy group, an alkylthio group, an acyloxy group, an amino group which may be substituted with an alkyl group or an amino protective group, a carboxyl group, an alkoxycarbonyl group, an aminocarbonyl group, or a cyano group); n is the integer selected from 0 to 6; Y is —C(O)—; and A is an aromatic heterocyclic ring including at least one or more nitrogen atom.

Further, as the heterocyclic compounds represented by the general formula (I) set out in claim 1 or pharmaceutically acceptable salt thereof, the following compounds are preferable.

Preferably, $R^1$ should be a cycloalkyl group having a substituent(s), more preferably a cyclopropyl group having a substituent(s), and most preferably either of a 2,2-dimethylcyclopropyl group, a 2,2-dichlorocyclopropyl group, a 2,2-difluorocyclopropyl group or a 2,2-dibromocyclopropyl group, Among them, 2,2-dimethylcyclopropyl group and 2,2-dichlorocyclopropyl group are especially preferred.

In the case where $R^1$ is a 2,2-dimethylcyclopropyl group having a substituent(s), preferably an absolute configuration of the carbon atom on the cyclopropyl group adjacent to the carbonyl group should be S.

Preferably $R^2$ should be a hydrogen atom or a methyl group, and more preferably hydrogen atom.

Preferably $R^3$ should be a hydrogen atom or a methyl group, and more preferably hydrogen atom.

Preferably $R^4$ should be a cycloalkyl group having a substituent(s) or an aryl group having a substituent(s), more preferably cyclopropyl group having a substituent(s), and most preferably either of a 2,2-dimethylcyclopropyl group, a 2,2-dichlorocyclopropyl group, a 2,2-difluorocyclopropyl group or a 2,2-dibromocyclopropyl group. Further, among them, 2,2-dimethylcyclopropyl group and 2,2-dichlorocyclopropyl group are especially preferred.

In the case where $R^4$ is a 2,2-dimethylcyclopropyl group having a substituent(s), preferably the absolute configuration of the carbon atom on the cyclopropyl group adjacent to the carbonyl group should be S.

Further, in the case where each of $R^1$ and $R^4$ is a 2,2-dimethylcyclopropyl group having a substituent(s), preferably the absolute configuration of the carbon atoms on the cyclopropyl group of $R^1$ adjacent to the carbonyl group should be S for both.

Preferably, A should be either of an aromatic heterocyclic ring or an aromatic heterocyclic ring having a substituent(s), and more preferably either of a pyridine, a pyridazine, a pyrimidine, a pyridine having a substituent(s), a pyridazine having a substituent(s) or a pyrimidine having a substituent (s).

Preferably, B should be either of an aromatic ring, an aromatic ring having a substituent(s), an aromatic heterocyclic ring or an aromatic heterocyclic ring having a substituent(s), and more preferably a benzene ring or a benzene ring having a substituent(s).

Preferably, X should be an interatomic bond, —O—, —O—CHR$^7$—, —CHR$^8$—O—, —S—, —NR$^3$, —CR$^{24}$R$^{25}$— or —O—CHR$^{30}$—CHR$^{31}$— wherin R$^7$, R$^8$, R$^{24}$, R$^{30}$ and R$^{31}$ are either of a hydrogen atom or an alkyl group; $R^{13}$ is either of a hydrogen atom, an alkyl group or an acyl group; and $R^{25}$ is a hydrogen atom, a hydroxy group, an alkyl group, an alkyl group having a substituent(s), a mercapto group, an alkoxy group, an alkylthio group, an acyloxy group, an amino group, an alkylamino group, an amino group substituted with an amino protective group, a carboxyl group, an alkoxycarbonyl group, an aminocarbonyl group, or a cyano group); and more preferably —X— should be —O—, —O—CHR$^7$—, —CHR$^8$—, —S—, —NR$^{13}$— or —CR$^{24}$R$^{25}$— wherein $R^7$, $R^8$ and $R^{24}$ are either of a hydrogen atom or an alkyl group; $R^{13}$ is either of a hydrogen atom, an alkyl group or an acyl group; and $R^{25}$ is a hydrogen atom, a hydroxy group, an alkyl group which may be substituted, a mercapto group, an alkoxy group, an alkylthio group, an acyloxy group, an amino group which may be substituted with an alkyl group or an amino protective group, a carboxyl group, an alkoxycarbonyl group, an aminocarbonyl group, or a cyano group.

Preferably, Y should be an interatomic bond, —CO—, —CONR$^5$—, —CSNR$^6$— or —SO$_2$— wherein R$^5$ a R$^6$ are a hydrogen atom or an alkyl group, and more preferably Y should be —CO—.

Further, in the present invention, $R^1$ and $R^4$ may be the same or different from each other, which may be either of a 2,2-dimethylcyclopropyl group, a 2,2-dichlorocyclopropyl group, a 2,2-difluorocyclopropyl group or a 2,2-dibromocyclopropyl group, and preferably —Y— should be —O— and n=0.

Further in the present invention, preferably $R^1$ should be either of a 2,2-dimethylcyclopropyl group, a 2,2-dichlorocyclopropyl group, a2,2-difluorocyclopropyl group or a 2,2-dibromolcyclopropyl group; $R^4$ should be an aryl group or an aryl group having a substituent(s);—Y— should be the —CO—; and n should be an integer selected from 1 to 3.

Further in the present invention, preferably $R^1$ should be either of a 2,2-dimethylcyclopropyl group, a 2,2-dichlorocyclopropyl group, a2,2-difluorocyclopropyl group or a 2,2-dibromocyclopropyl group; $R^4$ should be an aryl group or an aryl group having a substituent(s); —Y— should be an interatomic bond, and n should be an integer selected from 2 to 4.

Further in the present invention, a heterocyclic compound or a pharmaceutically acceptable salt thereof represented by any of the following formulas is preferred.

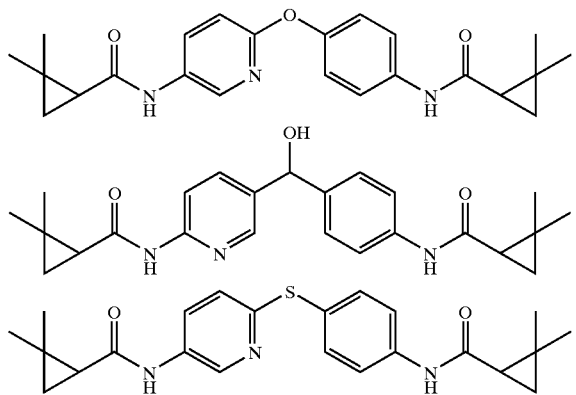

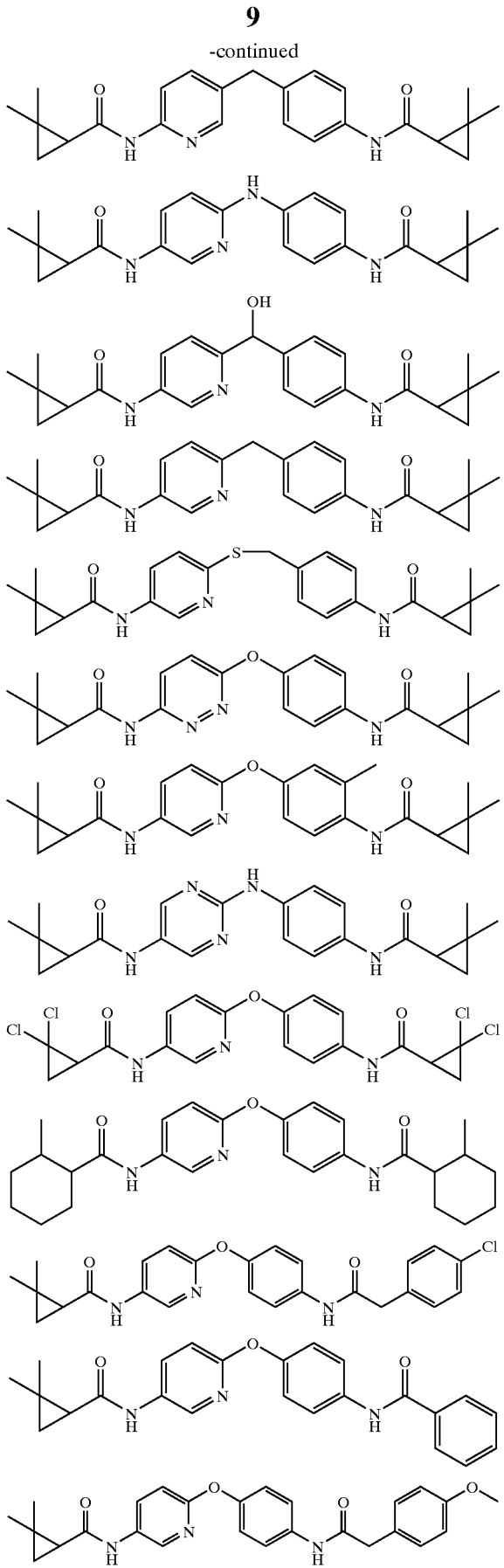

The pharmaceutically acceptable salt includes, for a sufficiently acidic compound according to the present invention, for example, an ammonium salt, an alkali metal salt (for example, a sodium salt and a potassium salt which are preferable) and an alkali earth metal salt (for example, a calcium salt and a magnesium salt which are preferable) of the compound, and for a salt of organic bases, for example, a dicyclohexylamine salt, a benzathine salt, a N-methyl-D-glucan salt, a hydramine salt and a salt of amino acid such as arginine or lysine. Further, for a sufficiently basic compound according to the present invention, the pharmaceutically acceptable salt specifically includes an acid added salt of the compound, for example, an inorganic acid salt such as hydrochloric acid, sulfuric acid, nitric acid and phosphoric acid, or an organic acid salt such as acetic acid, lactic acid, citric acid, tartaric acid, maleic acid, fumaric acid and monomethylsulfate. Further, depending on the case, the salt may includes a salt hydrate or a hydrate.

It is to be noted that the present invention should include all of the isomers such as an optical isomer and a geometric isomer, a hydrate, a solvate or a crystal form.

The compounds of the present invention can be synthesized by way of the following method.

For example, compounds of the present invention defined in (I) wherein X is an oxygen atom, Y is a carbonyl group, n=0, A is pyridine, B is benzene and $R^1$ and $R^4$ are the same, can be obtained by reacting corresponding diamine compounds with corresponding acid halide such as an acid chloride by 2 or more equivalents in the presence of base, or otherwise may be reacted with carboxylic acid by 2 or more equivalents in the presence of the condensation agent, as shown below, thereby obtaining the intended compound.

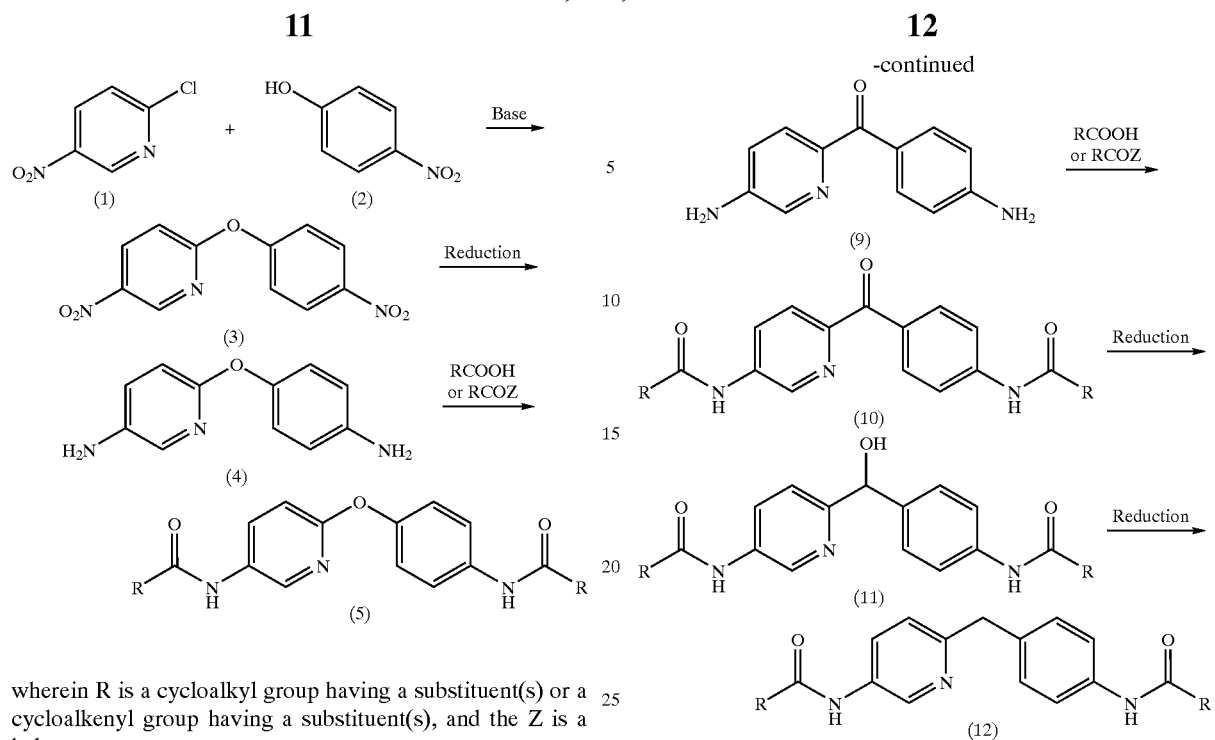

wherein R is a cycloalkyl group having a substituent(s) or a cycloalkenyl group having a substituent(s), and the Z is a halogen atom.

Further, by using the reaction shown above with small modification applied thereto, it will be also possible to synthesize a compound wherein X is a nitrogen atom or a sulfur atom, a compound wherein A is a heterocyclic ring other than pyridine, or a compound wherein B is an aromatic or a heterocyclic ring other than benzene ring.

For example, compounds of present invention defined in (I) wherein X is a carbon atom, Y is a carbonyl group, n=0, A is a pyridine, B is a benzene and $R^1$ and $R^4$ are the same, can be obtained by reacting corresponding diamine compounds with corresponding acid halide such as an acid chloride by 2 or more equivalents in the presence of base, or otherwise may be reacted with a carboxylic acid by 2 or more equivalents in the presence of a condensation agent, leading to a ketone body, which will be further reduced to an alcohol compound and the alcohol compound will be further reduced so as to synthesize a methylene body, as shown below.

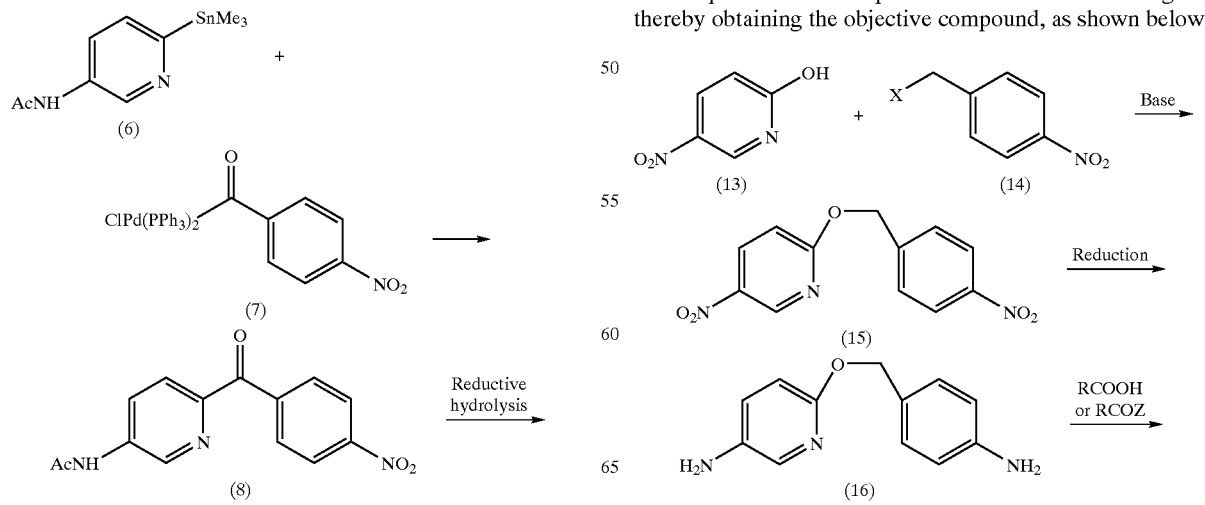

wherein R is a cycloalkyl group having a substituent(s) or a cycloalkenyl group having a substituent(s), and Z is a halogen atom.

Further, in the above reactions, a compound having different amide substituents at opposite ends can be synthesized by introducing sequentially the amide substituents by way of, for example, changing the sequence of the procedures after (XI) so that hydrolyzing may be practiced first to generate an amine compound, which will be precedently acylated.

For example, compounds of the present invention defined in (I) wherein —X— is —OCH$_2$—, Y is a carbonyl group, n=0, A is pyridine, B is benzene, and $R^1$ and $R^4$ are the same, can be obtained by reacting corresponding diamine compounds with corresponding acid halide such as an acid chloride by 2 or more equivalents in the presence of base, or otherwise may be reacted with a carboxylic acid by 2 or more equivalents in the presence of a condensation agent, thereby obtaining the objective compound, as shown below.

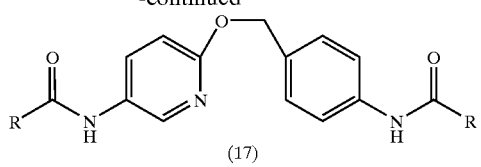

wherein R is a cycloalkyl group having a substituent(s) or a cycloalkenyl group having a substituent(s), X is a leaving group such as a halogen atom and Z is a halogen atom.

Further, by using the reaction shown above with small modification applied thereto, a compound wherein X is —OCH$_2$CH$_2$CH$_2$— or —SCH$_2$— can be synthesized For example, compounds of the present invention defined in (I) wherein —X— is —CH$_2$—, Y is a carbonyl group, n=0, A is a thiazole, B is benzene, and R$^1$ and R$^4$ are the same, can be obtained by reacting corresponding diamine compounds with corresponding acid halide such as an acid chloride by 2 or more equivalents in the presence of base, or otherwise may be reacted with a carboxylic acid by 2 or more equivalents in the presence of the condensation agent, thereby obtaining the objective compound, as shown below.

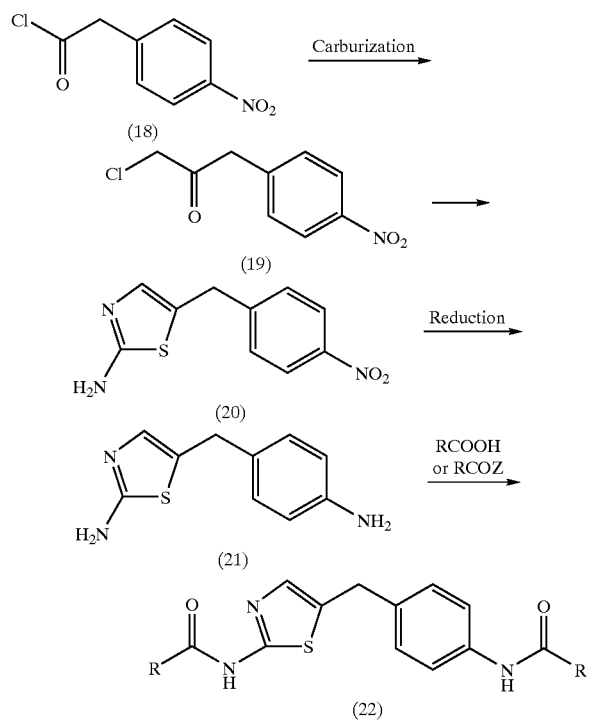

wherein R is a cycloalkyl group having a substituent(s) or a cycloalkenyl group having a substituent(s), and Z is a halogen atom.

For example, compounds of present invention defined in (I) wherein —X— is —CH$_2$—, Y is a carbonyl group, n=0, A is piperidine, B is benzene, and R$^1$ and R$^4$ are the same, can be obtained by reacting corresponding diamine compounds with corresponding acid halide such as an acid chloride by 2 or more equivalents in the presence of base, or otherwise may be reacted with a carboxylic acid by 2 or more equivalents in the presence of the condensation agent, thereby obtaining the objective compound, as shown below.

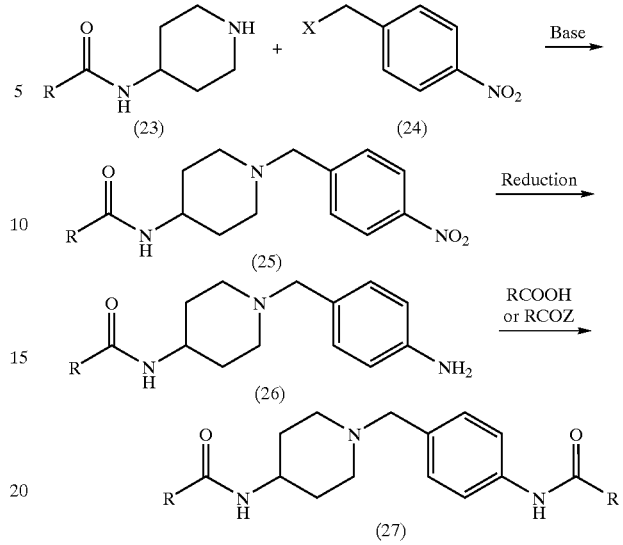

wherein R is a cycloalkyl group having a substituent(s) or a cycloalkenyl group having a substituent(s), X is a leaving group such as a halogen atom and Z is a halogen atom.

Further, by using the reaction shown above with small modification applied thereto, a compound wherein X of —CH$_2$CH$_2$— can be synthesized.

For example, compounds of the present invention defined in (I) wherein —X— is an oxygen atom, Y is a carbonyl group, n=0, A is pyridine, B is benzene, and R$^1$ and R$^4$ are different from each other, can be obtained by reacting, corresponding diamine compounds with corresponding acid halide such as an acid chloride by about one equivalent in the presence of base, or otherwise may be reacted with a carboxylic acid by about one equivalent in the presence of the condensation agent, thereby introducing a substituent(s) to one end of the diamine compound, and similarly the resultant compound may be additionally reacted with the acid halide or the carboxylic acid having a structure different from that of the acid halide or the carboxylic acid which has been used in the preceding stage so as to obtain the objective compound, as shown below.

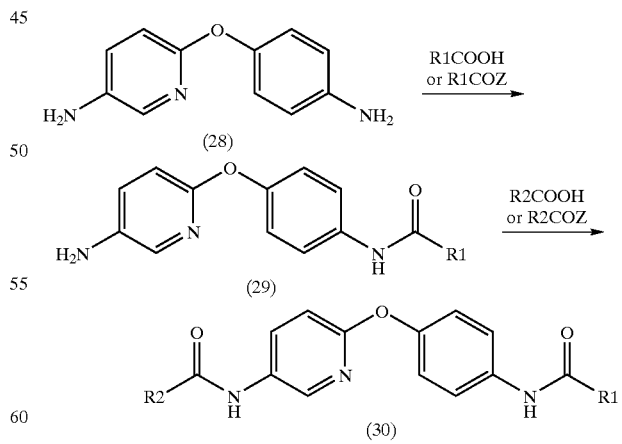

wherein R1 is an alkyl group, an alkyl group having a substituent(s), a cycloalkyl group, a cycloalkyl group having a substituent(s), a cycloalkenyl group, a cycloalkenyl group having a substituent(s), an aryl group, an aryl group having a substituent(s), a heterocyclic ring having one or more hetero atoms or a heterocyclic ring having one or more hetero atoms and a substituent(s); R2 is a cycloalkyl group having a substituent(s) or a cycloalkenyl group having a substituent(s); and Z is a halogen atom.

Further, a compound having $R^1$ different from $R^4$ can be synthesized by, for example, introducing an acyl group in incremental steps according to an alternative method as shown below.

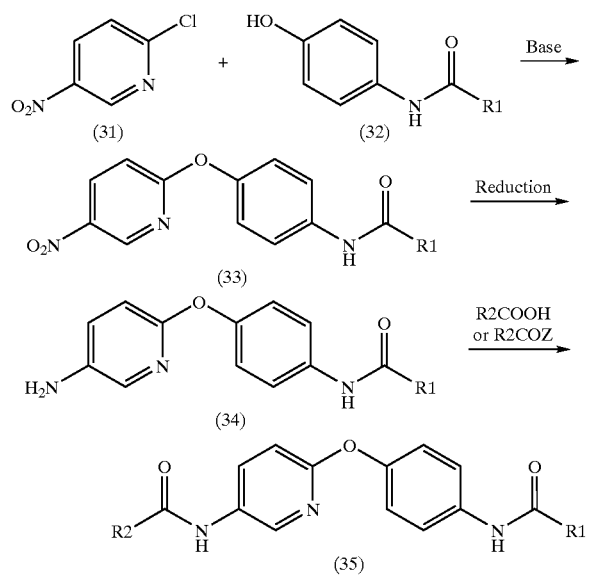

wherein R1 is an alkyl group, an alkyl group having a substituent(s), a cycloalkyl group, a cycloalkyl group having a substituent(s), a cycloalkenyl group, a cycloalkenyl group having a substituent(s), an aryl group, an aryl group having a substituent(s), a heterocyclic ring having one or more hetero atoms or a heterocyclic ring having one or more hetero atoms and a substituent(s); R2 is a cycloalkyl group having a substituent(s) or a cycloalkenyl group having a substituent(s); and Z is a halogen atom.

Further, a compound having $R^1$ different from $R^4$ can be synthesized also using such a method in which a substituent (s) for R1 may be introduced at the last stage by elaborating an amine protector as an intermediate, as shown below.

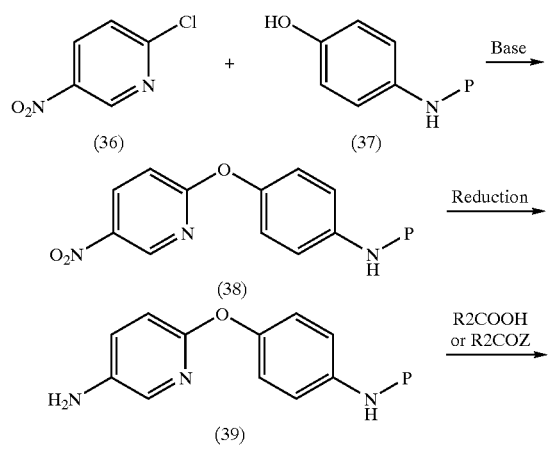

wherein R1 is an alkyl group, an alkyl group having a substituent(s), a cycloalkyl group, a cycloalkyl group having a substituent(s), a cycloalkenyl group, a cycloalkenyl group having a substituent(s), an aryl group, an aryl group having a substituent(s), a heterocyclic ring having one or more hetero atoms or a heterocyclic ring having one or more hetero atoms and a substituent(s); R2 is a cycloalkyl group having a substituent(s) or a cycloalkenyl group having a substituent(s); Z is a halogen atom; and P is an amino protective group.

For example, compounds of the present invention defined in (I) wherein X is an oxygen atom, Y is an interatomic bond, n=2, A is a pyridine and B is a benzene, can be obtained by reacting monoamide compounds with corresponding alkylating agent such as an alkyl halide in the presence of base, as shown below, thereby obtaining the objective compound.

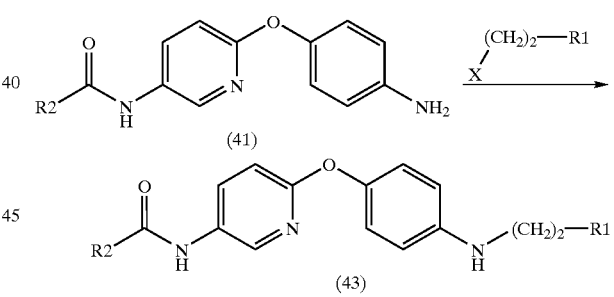

wherein R1 is an alkyl group, an alkyl group having a substituent(s), a cycloalkyl group, a cycloalkyl group having a substituent(s), a cycloalkenyl group, a cycloalkenyl group having a substituent(s), an aryl group, an aryl group having a substituent(s), a heterocyclic ring having one or more hetero atoms, or a heterocyclic ring having one or more hetero atoms and a substituent(s); and R2 is a cycloalkyl group having a substituent(s) or a cycloalkenyl group having a substituent(s).

To synthesize, for example, the compounds of the present invention defined in (I) wherein X is an oxygen atom, —Y— is —CONH—, —SO$_2$— or —COO—, n=0, A is a pyridine and B is a benzene, for example, monoamide compounds may be used as a starting material, and then they may be reacted respectively with the corresponding isocyanate, sulfonyl halide, or ester chlorocarbonate, as shown below, thereby obtaining the objective compound.

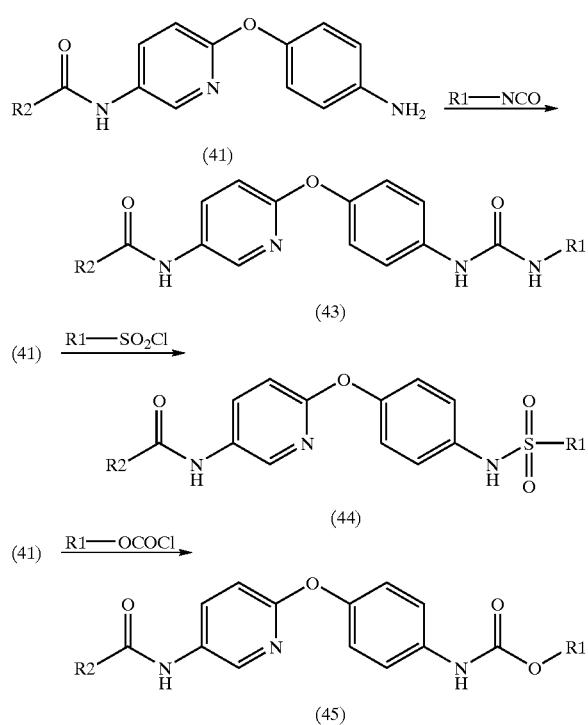

wherein R1 is an alkyl group, an alkyl group having a substituent(s), a cycloalkyl group, a cycloalkyl group having a substituent(s), a cycloalkenyl group, a cycloalkenyl group having a substituent(s), an aryl group, an aryl group having a substituent(s), a heterocyclic ring having one or more hetero atoms, or a heterocyclic ring having one or more hetero atoms and a substituent(s); and R2 is a cycloalkyl group having a substituent(s) or a cycloalkenyl group having a substituent(s).

Further, by using a reaction similar to the aforementioned reaction, a compound having —Y— of —CSNH— or —SO— may be synthesized.

It should be appreciated that those compounds of the present invention obtainable by the methods defined above can be refined by using the known technologies, including the extraction, distillation, crystallization or column chromatography, which have been normally used in the organic synthesis.

Those obtained compounds of the present invention, as will be described later, have an activity for inhibiting the AP-1 or NF-kappaB activation and thus are useful in providing the cure against the inflammatory diseases which might be developed by those transcription factors. That is, the compounds of the present invention are useful as an anti-inflammatory agent, an anti-rheumatism agent, an immunosuppressive agent, a cancer metastasis inhibitor, an antiviral agent or a curative agent for arterial sclerosis, advantageously without side effects such as hormone action, which can inhibit the transcription of genes of a plurality of inflammatory cytokines, matrix metalloproteases, inflammatory cell adhesion factors, and so on.

If the compound of the present invention is used as a drug such as the anti-inflammatory agent, it may be administered in the manners of an oral administration, an intravenous administration, a percutaneous administration and an administration by way of eye-instillation. A dosage should be different depending on the symptom, an age of a patient and the applied administration method, typically 1~3000 mg/kg/day.

The compound of the present invention can be formulated by the conventional method. The compound can be formulated as a drug product in the forms of, for example, an injection, a tablet, a granule, a fine granule, a powder, a capsule, a cream, a suppository and the like, wherein those formulation carriers are available for the drug product, including, for example, lactose, glucose, D-mannitol, starch, crystalline cellulose, calcium carbonate, kaolin, amylum, gelatin, hydroxypropylcellulose, hydroxypropylmethylcellulose, polyvinyl pyrrolidone, ethanol, carboxymethylcellulose, carboxymethyl cellulose calcium salt, magnesium stearate, talc, acetyl cellulose, saccharose, titanium oxide, benzoic acid, p-oxybenzoate ester, sodium dehydro acetate, gum arabic, tragacanth, methylcellulose, egg york, surfactant, sucrose, simple syrup, citric acid, distilled water, ethanol, glycerin, propylene glycol, macrogol, sodium monohydrogen phosphate, sodium dihydrogen phosphate, sodium phosphate, dextrose, sodium chloride, phenol, thimerosal, p-oxybenzoic ester and sodium hydrogensulfite, which will be mixed with the compound of the present invention in use depending on the form of the drug product.

Further, a content of an active constituent included in the drug product of the present invention may be varied in dependence on the form of the drug product and not specifically limited but typically in the range of 0.01~100 weight percent, preferably in the range of 1~100 weight percent.

The present invention will now be described in more detail with reference to examples, though the present invention is not limited to those.

EXAMPLE 1

Process 1: Synthesis of a Diamine Compound (4)

Potassium carbonate (55.2 g, 0.4 mol) was added into dimethylformamide (300 ml) solution including 2-chloro-5-nitropyridine (1) (31.7 g, 0.2 mmol) and 4-nitrophenol (2) (33.4 g, 0.2 mol), and stirred for 18 hours. After the reaction having been completed, the solution was poured into water (1.5 liter), and the separated-out solid was filtered and dried, thereby obtained a dinteo compound (3) (48.2 g, 92%). The obtained dinitro compound (3) (26.1 g, 0.1 mol) was dissolved into methanol (1.75 liter), into which in turn 10% palladium carbon (50% water content) (2.61 g) was added, and further hydrogen gas was blown, thus reduced under normal pressure. After the reaction having been completed, celite filtering was applied to remove the palladium carbon, and then, after the solvent having been evaporated, it was purified by using silica gel column chromatography (dichloromethane, methanol), thus obtained a diamine compound (4) (15.8 g, 79%).

1H-NMR (300 MHz, CDCl$_3$) δ=6.67 (2H, d, J=8.7 Hz), 6.68 (1H, d, J=8.7 Hz), 6.89 (2H, d, J=8.7 Hz), 7.04 (1H, dd, J=8.7, 3.0 Hz), 7.69 (1H, d, J=3.0 Hz).

MS(ESI) m/z 202(M+H)$^+$.

Process 2: Synthesis of a Compound of Example 1 (5:R=2, 2-dimethylcyclopropane)

The diamine compound (4) (2.035 g, 10 mmol) obtained in the process 1 was dissolved in dichloromethane (100 ml) and added with triethylamine (4 ml, 29 mmol) and 2,2-dimethylcyclopropanecarbonyl chloride (3.37 g, 25 mmol), which in turn was stirred at room temperature for 14 hours. After the reaction having been completed, the solvent was evaporated, and then extracted with ethyl acetate followed by washing, drying and concentration according to the conventional manner applied to the resultant, which was further purified by using silica gel column chromatography (ethyl acetate, hexane), thus obtained an objective compound of example 1 (2.77 g, 70%).

1H-NMR (300MHz, DMSO-d6), δ=0.75–0.82 (2H, m), 0.96–1.01 (2H, m), 1.13–1.18 (12H, m), 1.61–1.68 (2H, m), 6.93 (1H, d, J=8.7 Hz), 7.00 (2H, d, J=8.7), 7.60 (2H, d, J=8.7 Hz), 8.05 (1H, dd, J=8.7, 2.7 Hz), 8,31 (1H, d, J=2.7 Hz), 10.07 (1H, s), 10.22 (1H, s). MS(ESI) m/z 394(M+H)$^+$.

EXAMPLE 2

According to the same method as in example 1, a compound of example 2 was synthesized by using 4-nitrobenzenethiol and 2-chloro-5-nitropyridine as the starting materials.

1H-NMR (300 MHz, CDCl$_3$), δ=0.82–0.86 (2H, m), 1.17–1.26 (14H, m), 1.41–1.45 (2H, m), 6,87 (1H, d, J=8.7 Hz), 7.44 (2H, d, J=8.7 Hz), 7.52–7.55 (2H, m), 7.78–7.81 (2H, m), 7.86–7.88 (1H, m), 8.37 (1H, d, J=2.4 Hz). MS(ESI) m/z 410(M+H)$^+$.

EXAMPLE 3

Triethylamine (35 ml) was added into dimethylformamide (50 ml) including 2-chloro-5-nitropyridine (1) (9.5 g, 60 mmol) and para-phenylenediamine hydrochloride (10.9 g, 60 mmol), and stirred at the room temperature for 14 hours. After the reaction having been completed, the solution was poured into water, and the resultant solid was filtered and then N-(5-nitropyridin-2-yl) para-phenylenediamine was obtained as a brown solid. This solid was dissolved in ethanol (800 ml) and added with 5%-palladium carbon (2 g) so as to cause a hydrogen substitution, and then reduced at 70° C. under the normal pressure for 6 hours. After the reaction having been completed, the celite filtering was applied to remove the palladium carbon, and then it was washed by using a mixed solvent of ethyl acetate and hexane, thus obtained N-(5-amino-pyridin-2-yl) para-phenylenediamine (8.8 g, 75%).

Thereafter, according to the same method as of the process 2 in example 1, a compound of example 3 was obtained by using obtained diamine as the starting material.

1H-NHR (300 MHz, DMSO-d6) δ=0.70–0.80(2H, m), 0.93–0.99 (2H, m), 1.15 (12H, s), 1.58–1.66 (2H, m), 6.74 (1H, d, J=9.0 Hz), 7.44 (2H, d, J=9.0 Hz), 7.50 (2H, d, J=9.0 Hz), 7.77 (1H, dd, J=9.0, 2.7 Hz), 8.28 (1H, d, J=2.7 Hz), 8.77 (1H, s), 9.86 (1H, s), 9.92 (1H, s). MS(ESI) m/z 393(M+H)$^+$.

EXAMPLE 4

Process 1: Synthesis of 2-acetamide-5-trimethylstannylpyridine (6)

Triethylamine (1 ml, 7.2 mmol), acetic anhydride (0.6 ml, 6.35 mmol) and 4-dimethylaminopyridine (1 mg) were added into a dichloromethane (50 ml) solution of 2-amino-5-bromopyridine (1 g, 5.8 mmol) and stirred at the room temperature for 15 hours. After the reaction having been completed, the solvent was evaporated and the resultant solution was made acidic by hydrochloric acid, and then the resultant was extracted with ethyl acetate, washed, dried and concentrated according to the conventional manner, thus obtained 2-acetamide-5-bromopyridine (808 mg, 65%) as a white crystal. A toluene (3 ml) solution of this 2-acetamide-5-bromopyridine (30 mg, 0.14 mmol), hexamethylditin (110 mg, 0.336 mmol) and tetrakis (triphenylphosphine) palladium (10 mg, 0.01 mmol) was stirred at 100° C. under argon for 18 hours. After the reaction having been completed, the solid matter was filtered out, and the filtrate was extracted with ethyl acetate, and then after having been washed, dried and concentrated according to the conventional manner, it was purified by using the silica gel thin-layer chromatography (the ethyl acetate, hexane), thus obtained 2-acetamide-5-trimethylstannylpyridine (6) (10 mg, 23%).

1H-NMR (300 MHz, CDCl$_3$) δ=0.32 (9H, s), 2.20 (3H, s), 7.77 (1H, dd, J=8.1, 1.5 Hz), 8.14 (1H, d, J=8.1 Hz), 8.25 (1H, d, J=1.5 Hz). MS(ESI) m/z 301(M+H)$^+$.

Process 2: Synthesis of a Palladium Complex (7)

A benzene (50 ml) solution of 4-nitrobenzoyl chloride (926 mg, 5 mmol) and tetrakis (triphenylphosphine) palladium (2.89 g, 2.5 mmol) was stirred at the room temperature for 6 hours. After the completion of the reaction, the solvent was distilled out, and then the solution was washed by the ether thus obtained the palladium complex (7) in the form of a light orange crystal (2.08 g).

1H-NMR (300 MHz, CDCl), δ=7.21–7.39 (18H, m), 7.59–7.71 (14H, m), 7.80 (2H, d, J=9.0 Hz).

Process 3: Synthesis of Example 4 Compound (11:R=2,3-dimethylcyclopropane)

A toluene (20 ml) solution of the 2-acetamide-5-trimethylstannylpyridine (6) (100 mg, 0.336 mmol) obtained in the process 1 and the palladium complex (7) (390 mg, 0.48 mmol) obtained in the process 2 was stirred at 100° C. under argon for 2 hours. After the completion of the reaction, the solution was poured into diluted hydrochloric acid, extracted with ethyl acetate, and after having been washed, dried and concentrated according to the conventional manner, then purified by using silica gel chromatography (ethyl acetate, hexane), thus obtained objective material of 2-acetamide-5-(4-nitrophenylcarbonyl) pyridine (8) in the form of a light yellow crystal (18 mg, 20%).

The obtained 2-acetamide-5-(4-nitrophenylcarbonyl) pyridine (8) (18 mg, 0.063 mmol) and FeSO$_4$.7H$_2$O (200 mg, 0.72 mmol) were heated and refluxed for 10 minutes in the mixed solvent of water (4 ml) and ethanol (0.5 ml). Further, 100 mg of aqueous ammonia solution was added thereto and reflux was continued for another 20 minutes. After the reaction having been completed, the solid matter was filtered out, and the filtrate was extracted with ethyl acetate and then washed, dried and concentrated according to the conventional manner, thus obtained 2-acetamide-5-(4-aminophenylcarbonyl) pyridine in the form of a yellow oily matter (11 mg).

The obtained 2-acetamide-5-(4-aminophenylcarbonyl) pyridine (20 mg) was stirred at 70° C. in 4M hydrochloric acid (3 ml) for 2 hours. After the reaction was completed, the resultant was extracted with ethyl acetate, and then washed, dried and concentrated according to the conventional manner, purified by using silica gel thin-layer chromatography (ethyl acetate), thus obtained 2-amino-5-(4-aminophenylcarbonyl) pyridine (9) (5 mg) in the form of a light yellow crystal.

4-dimethylaminopyridine (0.5 mg) and 2,2-dimethylcyclopropane-carbonyl chloride (28 mg, 0.2 mmol) was added to a pyridine (3 ml) solution of the obtained 2-amino-5-(4-amino-phenylcarbonyl) pyridine (9) (5 mg, 0.0022 mmol), and stirred at the room temperature for 3 hours. After the completion of the reaction, the solution was extracted with ethyl acetate, and then washed, dried and concentrated according to the conventional manner, thus obtained a diamide compound (10:R=2,2-dimethylcyclopropane) in the form of a yellow oily matter (15 mg).

Sodium borohydride (3 mg) was added to an ethanol (3 ml) solution of the obtained diamide compound (10:R=2,2-dimethylcyclopropane) (14 mg) and stirred at the room temperature for 2 hours. After the completion of the reaction, the solvent was distilled out, and then purified by using silica gel thin-layer chromatography (ethyl acetate, hexane), thus obtained an alcohol compound (11:R=2,2-dimethylcyclopropane) (5 mg) of the objective compound of example 4.

1H-NMR (300 MHz, CDCl$_3$) δ=0.80–0.92 (2H, m), 1.15–1.24 (14H, m), 1.37–1.47 (2H, m), 5.80 (1H, s), 7.28 (2H, d,J=8.7 Hz), 7.35–7.43 (1H, brs), 7.49 (2H, d, J=8.7 Hz), 7.60–7.67 (1H, m), 8.14 (1H, d, J=8.7 Hz), 8.19–8.23 (1H, m), 8.30–8.40 (1H, brs). MS(ESI) m/z 408(M+H)$^+$.

EXAMPLE 5

20%-palladium hydroxide on carbon (1 mg) and 4M hydrochloric acid (50 mg) were added to an ethanol solution (2 ml) of the alcohol compound obtained in example 4 (11:R=2,2-dimethylcyclopropane) (3 mg), and then the solution was subjected to the hydrogen substitution and stirred at 50° C. for 4 hours. After the reaction having been completed, the solid matter was filtered out, and the filtrate was extracted with ethyl acetate and further washed, dried and concentrated according to the conventional manner, followed by the purification with the silica gel chromatography (ethyl acetate, hexane), thus obtained a methylene compound of the objective compound of example 5 (12:R=2,2-dimethylcyclopropane) (1 mg).

1H-NMR (300 MHz, CDCl$_3$), δ=0.80–0.90 (2H, m), 1.21–1.28 (14H, m), 1.34–1.42 (2H, m), 3.88 (2H, s), 7.06–7.13 (4H, m), 7.40–7.49 (4H, m), 8.06–8.12 (1H, m). MS(ESI) m/z 392(M+H)$^+$.

EXAMPLE 6

Process 1: Synthesis of 5-acetamide-2-trimethylstannylpyridine

An acetic acid solution (80 ml) of 2-bromo-5-nitropyridine (3 g, 14.8 mmol) and iron (25 g, 446 mmol) was stirred at the room temperature for 15 hours. After the reaction was completed and the solvent was distilled out, the resultant was extracted by using ethyl acetate, and then further washed, dried and concentrated according to the conventional manner, thus obtained 5-amino-2-bromopyridine (2.26 g, 89%) as a white crystal.

To an acetic anhydride solution (1.5 ml) of the obtained 5-amino-2-bromopyridine (1.75 g, 10.2 mmol), pyridine (3 ml) was added and stirred at the room temperature for 6 hours. After the reaction having been completed, the solvent was distilled out, and the resultant was extracted with ethyl acetate and washed, dried and concentrated according to the conventional manner, thus obtained 5-acetamide-2-bromopyridine (2.135 g, 98%) in the form of a white crystal.

A toluene (100 ml) solution of the obtained 5-acetamide-2-bromopyridine (1.3 g, 6 mmol), hexamethylditin (5 g, 15.3 mmol) and tetrakis (triphenylphosphine) palladium (1 g, 0.87 mmol) was stirred at 100° C. under the argon atmosphere for 6 hours. After the reaction having been completed, the solid matter was filtered out and the filtrate was extracted with ethyl acetate, and washed, dried and concentrated according to the conventional manner, followed by the purification by using silica gel chromatography (ethyl acetate, hexane), thus obtained 5-acetamide-2-trimethylstannylpyridine (1.45 g, 80%).

1H-NMR (300 MHz, CDCl$_3$), δ=0.33 (9H, s), 2.19 (3H, s), 7.68 (1H, d, J=7.8 Hz), 8.04(1H, dd, J=7.8,2.4 Hz), 8.66(1H, d, J=2.4 Hz). MS(ESI) mz 301M+H)$^+$.

Then, according to the same method as that in the process 3 of example 4, a compound of example 6 was synthesized by using the above 5-acetamide-2-trimethylstannylpyridine and the palladium complex obtained in the process 2 compound of example 4 (7) as a starting material.

1H-NMR (300 MHz, CDCl$_3$), δ=0.78–0.91 (2H, m), 1.16–1.26 (14H, m), 1.36–1.46 (2H, m), 5.68 (1H, s), 7.03–7.10 (1H, m), 7.22–7.31 (2H, m), 7.38–7.52 (2H, m), 7.94–8.02 (1H, m), 8.51–8.57 (1H, m). MS(ESI) m/z 408 (M+H)$^+$.

EXAMPLE 7

According to the same method as of example 5, a compound of example 7 was synthesized by using example 6 compound as a starting material.

1H-NMR (300 MHz, CDCl$_3$) δ=0.78–0.92 (2H, m), 1.16–1.28 (14H, m), 1.35–1.46 (2H, m), 4.06 (2H, s), 7.05 (1H, d, J=8.7 Hz), 7.16 (2H, d, J=7.8 Hz), 7.27–7.36 (1H, m), 7.37–7.50 (3H, m), 8.02–8.09 (1H, m), 8.44 (1H, d, J=2.7 Hz). MS(ESI) m/z 392(M+H)$^+$.

EXAMPLE 8

Process 1: Synthesis of 3-amino-6-(4-nitrophenoxy) pyridazine 3-amino-6-chloropyridazine (520 mg, 4 mmol) and 4-nitrophenol (1.39 g, 10 mmol) were suspended in a 1M sodium hydroxide aqueous solution (10 ml) and heated in a sealed tube at 160° C. for 18 hours. After the reaction was completed, dichloromethane (30 ml) was added to thereto for extraction, and after the organic layer was washed with 1M sodium hydroxide aqueous solution (10 ml), the resultant was dried with sodium sulfide. After the solvent was distilled out, the resultant was purified by using a silica gel TLC plate (dichloromethane, methanol), thus obtained 3-amino-6-(4-nitro-phenoxy) pyridazine (69 mg, 7%).

1H-NMR (300 MHz, DMSO-d6) δ=6.42 (2H, s), 6.99 (1H, d, J=9.3 Hz), 7.25 (1H, d, J=9.6 Hz), 7.27 (2H, d, J=9.3 Hz), 8.26 (2H, d, J=9.0 Hz). MS(ESI) m/z 233(M+H)$^+$.

Process 2: Production of 3-amino-6-(4-aminophenoxy) pyridazine

FeSO$_{4.}$7H$_2$O (834 mg, 3 mmol) was added into a mixed solvent of ethanol (1 ml) and water (5 ml) of the pyridazine obtained in the process 1, and stirred at 100° C. for 10 minutes, and after the solution having been cooled to the room temperature, ammonia water (0.25 ml) was added thereto. The resulting black tarry substance was subjected to decantation with ethyl acetate (5 times, each by 5 ml), and after the ethyl acetate solution having been collected, it was washed with water and dried with sodium sulfide. After the solvent having been distilled out, the resultant was purified by using a silica gel TLC plate (dichloromethane, methanol), thus obtained 3-amino-6-(4-aminophenoxy) pyridazine (23 mg, 57%).

1H-NMR (300 MHz, DMSO-d6) δ=4.92 (2H, s), 6.05 (2H, s), 6.55 (2H, d, J=8.7 Hz), 6.75 (2H, d, J=8.7 Hz), 6.87 (1H, d, J=9.3 Hz), 6.96 (1H, d, J=9.3 Hz). MS(ESI) m/z 203(M+H)$^+$, 405(2M+H)$^+$.

Process 3: Synthesis of Example 8 Compound

An acetonitrile (2 ml) solution of the diamine compound (23 mg, 0.11 mmol) obtained in the process 2 was added with pyridine (0.05 ml, 0.5 mmol) under the ice-water cooling and further added with 2,2-dimethylcyclopropanecarbonyl chloride (45 mg, 0.33 mmol), and then stirred at the room temperature for 15 minutes. After water (0.03 ml) was added thereto, the solvent was distilled out therefrom and purified by using a silica gel TLC plate (dichloromethane, methanol), thus obtained compound of example 8 (30 mg, 70%).

1H-NMR (300 MHz, DMSO-d6) δ=0.79–0.89 (2H, m), 0.97–1.05 (2H, m), 1.17–1.21 (12H), 1.66 (2H, dd, J=8.1, 5.1 Hz), 1.91 (1H, dd, J=7.8, 5.7 Hz), 7.11 (2H, dd, J=6.9, 2.4 Hz), 7.40 (1H, d, J=9.6 Hz), 7.64 (2H, d, J=9.0 Hz), 8.35 (1H, d, J=9.6 Hz), 10.12 (1H, s), 11.13 (1H, s). MS(ESI) m/z 395(M+H)$^+$.

EXAMPLE 9

Process 1:

A dimethylformamide (25 ml) suspension of 2-amino-5-nitropyridine (703 mg, 5 mmol), 1-iodo-4-nitrobenzene (1.25 g, 5 mmol), copper (34 mg, 0.5 mmol) and potassium carbonate (1.38 g, 10 mmol) was stirred at 100° C. for 13 hours. After the reaction having been completed, the extraction was applied to the solution by adding dichloromethane (200 ml) and water (100 ml), and after the organic layer having been washed with water (100 ml) by three times, it was dried with magnesium sulfate and concentrated. The concentrate was dissolved into tetrahydrofuran (50 ml) and concentrated, and then added with dichloromethane (20 ml) and n-hexane (20 ml) so to be crystallized, thus obtained a dinitro compound (0.90 g, 69%).

1H-NMR (300 MHz, DMSO-d6) δ=8.07 (2H, d, J=9.3 Hz), 8.28 (2H, d, J=9.3 Hz), 9.35(2H, s), 11.41(1H, s).

Process 2:

The dinitro compound obtained in the process 1, (506 mg, 2 mmol) was dissolved into acetonitrile (50 ml) and tetrahydrofuran (25 ml), which in turn was mixed with 10%-palladium carbon (283 mg) to cause the hydrogen substitution, and reduced under normal pressure. After the reaction having been completed, the sellaite filtering was used to remove the palladium carbon and the solvent was distilled out, thus obtained the diamine compound (0.38 g, 98%).

1H-NMR (300 MHz, DMSO-d6) δ=4.56 (2H, brs), 4.57 (2H, brs), 6.47 (2H, d, J=8.4 Hz), 7.26 (2H, d, J=8.7 Hz), 7.86 (2H, s), 8.35 (1H, s).

Process 3:

An acetonitrile (10 ml) solution of the diamine compound (102 mg, 0.5 mmol) was added with pyridine (0.10 ml, 1 mmol) under the ice-water cooling and further added with 2,2-dimethylcyclopropanecarbonylchloride (143 mg, 1 mmol), and then stirred at the room temperature for 20 hours. After water (1 ml) having been added thereto, the solvent was distilled out therefrom and a silica gel TLC plate (dichloromethane, methanol) was used for purification, and thus example 9 compound (150 mg, 75%) was obtained.

1H-NMR (300 MHz, DMSO-d6) δ=0.75 (1H, dd, J=8.1 Hz, J=3.9 Hz), 0.81 (1H, dd, J=7.7 Hz, J=3.8 Hz), 0.93–1.01 (2H, m), 1.14–1.19 (12H, s), 1.63 (2H, dd, J=8.0 Hz, J=5.3 Hz), 7.74 (2H, d, J=9.0 Hz), 7.60 (2H, d, J=9.0 Hz), 8.61 (2H, s), 9.40 (1H, s), 9.91 (1H, s), 10.07 (1H, s). MS(ESI) m/z 394(M+H)+.

EXAMPLE 10

Process 1: Synthesis of 1-hydroxy-3-(4-nitrophenyl)-2-propanone 4-nitrophenylacetic acid (1.00 g, 6 mmol) was added into a dichloromethane solution of oxalyl chloride (11 mmol, 11 ml) and stirred at a temperature range of room temperature to 40° C. for 4.5 hours. A crystal of acid chloride, which had been obtained by distilling out the solvent, was added with tris (trimethylsilyloxy)ethylene (4.6 ml, 14 mmol) and further added with 6 drops of SnCl4 under water cooling, and then stirred at the room temperature for 15 hours. The resultant was added with 1,4-dioxane (10 ml) and 1M hydrochloric acid (5 ml), and stirred at the room temperature for 30 minutes and at 90° C. for another 30 minutes. After cooling, dichloromethane (10 ml) and water (10 ml) were added into it to wash, and further the organic layer was washed with a saturated sodium hydrogencarbonate. Also, each of the aqueous layers was re-extracted with dichloromethane (20 ml) by one time for each so as to be mixed with the organic layer. The recovered organic layer was dried with magnesium sulfate, and the solvent was distilled out, thus obtained 1-hydroxy-3-(4-nitrophenyl)-2-propanone (579 mg, 54%).

1H-NMR (300 MHz, CDCl3) δ=2.93 (1H, t, J=3.9 Hz), 3.86 (2H, s), 4.37 (2H, d, J=3.9 Hz), 7.41 (2H, d, J=8.7 Hz), 8.22 (2H, d, J=8.7 Hz).

Process 2: Synthesis of 1-chloro-3-(4-nitrophenyl)-2-propanone (19)

An acetonitrile (4 ml) solution of the compound obtained in the process 1 (120 mg, 0.6 mmol) was added with pyridine (0.055 ml, 0.7 mmol), thionyl chloride (0.045 ml, 0.7 mmol) and 1 drop of dimethylformaldehyde under water cooling, and after having been stirred at 40° C. for 3 hours, it was further added with pyridine (0.025 ml, 0.3 mmol) and thionyl chloride (0.020 ml, 0.3 mmol) and stirred. After the reaction having been completed, the solvent was distilled out, and the resultant was purified with a silica gel TLC plate (n-hexane, ethyl acetate), thus obtained 1-chloro-3-(4-nitrophenyl)-2-propanone (19:115 mg, 88%).

1H-NMR (300 MHz, CDCl3) δ=4.07 (2H, s), 4.15 (2H, s), 7.40 (2H, d, J=8.7 Hz), 8.22 (2H, d, J=8.7 Hz). MS(ESI) m/z 212(M−H)−.

Process 3: Synthesis of 2-amino-5-(4-nitrobenzyl)-thiazole (20)

Thiocarbamide (54 mg, 0.7 mmol) was added to an ethanol (9 ml) suspension of the chloro compound (19) (150 mg, 0.7 mmol) obtained in the process 2 and stirred at 60° C. for 7 hours. After the solvent having been distilled out, the obtained crystal was washed with acetonitrile, thus obtained 2-amino-5-(4-nitrophenylbenzyl)thiazole (20) (135 mg, 82%).

1H-NMR (300 MHz, DMSO-d6) δ=4.04 (2H, s), 6.56 (1H, s), 7.56 (2H, d, J=9.0 Hz), 8.21 (2H, d, J=8.4 Hz). MS(ESI) m/z 236(M+H)+.

Process 4: Synthesis of 2-amino-5-(4-aminobenzyl)-thiazole (21)

The thiazole (20) (123 mg, 0.5 mmol) obtained in the process 3 was added to an acetic acid (10 ml) suspension of zinc (1.03 g, 16 mmol), which had been washed and activated by 1M hydrochloric acid, and stirred at the room temperature for 30 minutes. After the zinc having been filtered out, the filtrate was poured into an aqueous solution of dichloromethane (100 ml) and 2M sodium hydroxide aqueous solution (78 ml) under the ice water cooling. This organic layer and another organic layer, which was obtained by applying another extraction with the dichloromethane (totally 105 ml) to the aqueous layer, were mixed, and then the mixture was dried with sodium sulfate, and the solvent was distilled out, thus obtained 2-amino-5-(4-aminobenzyl) thiazole (21) (89 mg, 83%).

1H-NMR (300 MHz, DMSO-d6) δ=3.52 (2H, s), 4.82 (2H, s), 5.99 (1H, s), 6.47 (2H, d, J=8.4 Hz), 6.75 (2H, s),6.86 (2H, d, J=8.1 Hz). MS(ESI) m/z 206(M+H)+.

Process 5: Synthesis of a Compound of Example 10

A dichloromethane (12 ml) suspension of the thiazole (21) (60 mg, 0.3 mmol) obtained in the process 4 was added with pyridine (0.060 ml, 0.7 mmol) under water cooling and further added with 2,2-dimethylcyclopropanecarbonylchloride (146 mg, 1.1 mmol), and then stirred at the room temperature. After 3 hours, water (10 ml) was added into the solution for washing. The organic layer was dried with magnesium sulfate, and then the oil obtained by distilling out the solvent was purified by using a silica gel TLC plate (n-hexane, ethyl acetate), thus obtained example 10 compound (60 mg, 50%).

1H-NMR (300 MHz, CDCl3) δ=0.74 (1H, dd, J=7.8, 3.6 Hz), 0.86 (1H, dd, J=7.8, 3.9 Hz), 0.94 (1H, dd, J=5.4, 3.6 Hz), 0.99 (1H, dd, J=5.1, 3.6 Hz). 1.09 (3H, s), 1.11 (3H, s), 1.12 (3H, s), 1.13 (3H, s), 1.61 (1H, dd, J=7.8, 5.4 Hz), 1.74 (1H, dd, J=7.8, 5.4 Hz), 6.70 (1H, s), 7.11 (2H, d, J=8.4 Hz), 7.47 (2H, d, J=8.4 Hz), 9.96 (1H, s), 12.15 (1H, s). MS(ESI) m/z 398(M+H)$^+$.

EXAMPLE 11

According to the same method as that used in the process 2 of example 1, a compound of example 11 was synthesized by using 5-amino-2-(4-aminophenyl) pyridine as a starting material.

1H-NMR (300 MHz, CDCl$_3$) δ=0.80–0.91 (2H, m), 1.16–1.30 (14H, m), 1.38–1.48 (2H, m), 7.30–7.72 (5H, m), 7.90 (2H, d, J=8.4 Hz), 8.22–8.30 (1H, m), 8.52–8.55 (1H, m). MS(ESI) m/z 378(M+H)$^+$.

EXAMPLE 12

A dimethylformamide (10 ml) solution of 2-hydroxy-5-nitropyridine (13) (700 mg, 5 mmol) was added with sodium hydride (240 mg, 12 mmol) and further added with 4-nitrobenzylbromide (14:X=Br) (1.08 g, 5 mmol), and then stirred at the room temperature for 20 hours. After the reaction having been completed, the solution was extracted with ethyl acetate, washed, dried and concentrated according to the conventional manner, followed by the purification by using silica gel chromatography (dichloromethane, ethyl acetate), thus obtained the dinitro compound (15). This dinitro compound (15) was dissolved into an ethanol (50 ml), which was in turn added with 5%-palladium carbon (100 mg) to perform the hydrogen substitution and then reduced under the normal pressure. After the reaction having been completed, the palladium carbon was removed by the celite filtering, and after the solvent was distilled out, the resultant was purified by way of silica gel column chromatography (ethyl acetate), thus obtained the diamine compound (16) (430 mg, 40%).

Then, according to the same method as that used in the process 2 of example 1, example 12 compound was synthesized by using the diamine compound (16) as a starting material.

1H-NMR (300 MHz, DMSO-d6) δ=0.73–.80 (2H, m), 0.90–1.00 (2H, m), 1.10–1.19 (12H, m), 1.50–1.58 (1H, m), 1.60–1.68 (1H, m), 4.97 (1H, d, J=12.4 Hz), 5.30 91H, d, J-12.4 Hz), 6.43 (1H, d, J=9.9 Hz), 7.20 (2H, d, J=8.4 Hz), 7.41 (1H, dd, J=9.9, 3.0 Hz), 7.54 (2H, d, J=8.4 Hz), 8.12 (1H, d, J=3.0 Hz), 9.82 (1H, brs), 10.08 (1H, brs).

MS(ESI) m/z 408(M+H)$^+$.

EXAMPLE 13

According to the same method as example 12, a compound of example 13 was synthesized by using 2-hydroxy-5-nitropyridine and 2-(4-nitrophenyl)ethyl bromide as a starting material.

1H-NMR (300 MHz, DMSO-d6) δ=7.30–0.80 (2H, m), 0.90–0.99 (2H, m), 1.10–1.18 (12H, m), 1.50–1.58 (1H, m), 1.60–1.67 (1H, m), 2.84 (2H, t, J=7.5 Hz), 4.02 (2H, t, J=7.5 Hz), 6.38 (1H, d, J=9.6 Hz), 7.11 (2H, d, J=8.7 Hz), 7.37 (1H, dd, J=9.6, 3.0 Hz), 7.50 (2H, d, J=8.7 Hz), 8.01 (1H, d, J=3.0 Hz), 9.75 (1H, s), 10.00 (1H, s).

MS(ESI) m/z 422(M+H)$^+$.

EXAMPLE 14

Process 1:

A dimethylformamide (20 ml) solution of 2-mercapto-5-nitro-pyridine (1.56 g, 10 mmol) was added with 60% sodium hydride (446 mg, 11 mmol) and further added with 1-bromomethyl-4-nitrobenzene (2.14 g, 10 mmol), and then stirred at the room temperature for 1.5 hours. The reacted mixture was added into water (100 ml) to precipitate solid matter and the solid matter was filtered. The solid matter was added with dichloromethane (100 ml) to be dissolved therein, and washed with water (60 ml). This organic layer and another organic layer, which was obtained by applying 2 times of extraction with the dichloromethane (20 ml) to the aqueous layer, were mixed, and after having been dried with magnesium sulfate, distilled out the solvent, thus obtained a dinitro compound (2.51 g, 87%).

1H-NMR (300 MHz, DMSO-d6) δ=4.68 (2H, s), 7.62 (1H, dd, J=8.9 Hz, J=0.8 Hz), 7.74 (2H, d, J-8.7 Hz), 8.17 (2H, d, J=8.7 Hz), 8.39 (1H, dd, J=9.0 Hz, J=2.7 Hz), 9.25 (1H, dd, J=2.9 Hz, J=0.8 Hz).

Process 2:

A tetrahydrofuran (1.5 ml) solution of the dinitro compound (218 mg, 0.7 mmol) was added to an acetic acid (10 ml) suspension of zinc (1.36 g, 21 mmol), which had been washed and activated with 1M hydrochloride, and then stirred at the room temperature for 16 hours. After the zinc having been filtered out, the filtrate was poured into an aqueous solution of ethyl acetate (100 ml) and 2M sodium hydrate (110 ml) under the ice water cooling. The organic layer was washed with water (50 ml) and thereafter dried with magnesium sulfate so as to distill out the solvent. The concentrate was added with dichloromethane (50 ml) so as to be dissolved therein and then washed with an aqueous solution of 1M sodium hydroxide (30 ml) and water (30 ml), and after the organic layer was dried with the magnesium sulfate to distill out the solvent, the resultant was purified by using silica gel TLC plate (hexane, ethyl acetate), thus obtained a mixture including a diamine compound. A dichloromethane (10 ml) solution of this mixture (66 mg) was added with triethylamine (0.085 ml, 0.6 mmol) under the ice water cooling and further added with 2,2-dimethylcyclopropanecarbonylchloride (85 mg, 0.6 mmol), and then stirred at the room temperature for 17 hours. After water (10 ml) having been added into the resultant solution, the organic layer was dried with the magnesium sulfate to distill out the solvent, the resultant was purified with a silica gel TLC plate (dichloromethane, methanol), thus obtained example 14 compound (18 mg) of the target.

1H-NMR (300 MHz, DMSO-d6) δ=0.73–0.84 (2H, m), 0.93–1.02 (2H, m), 1.12–1.18 (12H, s), 1.59–1.68(2H, m), 4.3 (2H, s), 7.23 (1H, d, J=8.7 Hz), 7.27 (2H, d, J=9.0 Hz), 7.49 (2H, d, J=8.1 Hz), 7.89 (1H, dd, J=8.7 Hz, J=2.7 Hz), 8.66 (1H, d, J=2.7 Hz), 10.03 (1H, s), 10.23 (1H, s). MS(ESI) m/z 424(M+H)$^+$.

EXAMPLE 15

Process 1:

4-amino-1-benzylpiperidine (100 mg, 0.526 mmol) was dissolved into dichloromethane (10 ml) and then added with triethylamine (150 mg, 1.5 mmol) and 2,2-dimethylcyclopropanecarbonylchloride (159 mg, 1.2 mmol), which was further stirred at the room temperature for 14 hours. After the reaction was completed, the resultant was extracted with ethyl acetate and then washed, dried and concentrated according to the conventional manner and purified by using silica gel column chromatography (ethyl acetate, hexane), thus obtained a white crystal of 4-(2,2-dimethylcyclopropanecarbonylamino)-1-benzylpiperidine. The white crystal was dissolved into an ethanol (10 ml)-ethyl acetate (1 ml) mixed solvent, wherein 5% palladium carbon (150 mg) and formic acid (160 mg) were dissolved into the ethanol (10 ml) and applied thereto with dropping, which was stirred at the room temperature over night. After the palladium was filtered, the solvent was distilled out and aqueous solution of 2M sodium hydroxide was added therein to make pH>13, the solution was extracted with dichloromethane and further washed with a saturated saline solution, dried and vacuum concentrated, thus obtained 4-(2,2-dimethylcyclopropanecarbonylamino)piperidine (23:R =2,2-dimethylcyclopropane) (11.2 mg, 11%).

1H-NMR (300 MHz, CDCl$_3$) δ=0.68–0.72 (1H, m), 1.06–1.09 (1H, m), 1.13–1.38 (7H, m), 1.78 (2H, s), 1.88–1.97 (2H, m), 2.69 (2H, t, J=12.6 Hz), 3.06 (2H, td, J=3.3, 12.6 Hz), 3.88–3.95 (1H, m), 5.49 (1H, s). MS(ESI) m/z 197(M+H)$^+$.

Process 2:

4-nitrobenzyl bromide (24:X=Br) (110 mg, 0.5 mmol), potassium carbonate (352 mg, 2.55 mmol) and sodium iodide (76.5 mg, 0.5 mmol) were added to a dimethylformamide (5mil) solution of the piperidine (23) obtained in the process 1, and then stirred under the argon atmosphere at the room temperature for 2 hours. This was further stirred at 70° C. for 1 hour and was extracted with hexan-ethyl acetate (3:1) mixed solvent, and then washed with water and saturated saline solution, dried and vacuum concentrated, thus obtained a 4-nitrobenzylpiperadine compound (25:R=2,2-dimethylcyclopropane) in the form of a yellow crystal (95 mg, 57%).

1H-NMR (300 MHz, CDCl$_3$) δ=0.69–0.73 (1H, m), 1.07 (1H, t, J=4.8 Hz), 1.13 (3H, s), 1.15 (3H, s), 1.19–1.24 (1H, m), 1.41–1.49 (1H, m), 1.93 (2H, brs), 2.12–2.21 (2H, m), 2.78 (2H, d, J=11.7 Hz), 3.58 (2H, s), 3.75–3.88 (1H, m), 5.42–5.46 (2H, m, 7.50 (2H, d, J=8.4 Hz), 8.17 (2H, d, J=8.4 Hz). MS(ESI) m/z 332 (M+H)$^+$.

Process 3:

An acetic acid (3 ml) solution of the 4-nitrobenzylpiperidine compound (25) (65.8 mg, 0.2 mmol) obtained in the process 2 was added with zinc (300 mg) little by little at 0° C. After having been stirred at the room temperature for 2 hours, this was filtered to be taken out, had the solvent distilled out and neutralized with 2M aqueous sodium hydroxide, and then was extracted with ethylacetate. The resultant was washed with water and the saturated saline solution, dried and then vacuum concentrated, thus obtained a 4-aminobenzylpiperidine compound (26:R=2,2-dimethylcyclopropane) in the form of a yellow oily matter (50 mg, 85%).

1H-NMR (300 MHz, CDCl$_3$) δ=0.67–0.73 (1H, m), 1.07–1.25 (8H, m), 1.44–1.55 (2H, m), 1.89 (2H, brs), 2.05–2.15 (2H, m), 2.82–2.86 (2H, m), 3.44 (2H, s), 3.70 (1H, brs), 4.48 (1H, s), 6.64 (2H, d, J=8.4 Hz), 7.08 (2H, d, J=8.4 Hz). MS(ESI) m/z 302 (M+H)$^+$.

Process 4:

The 4-aminobenzylpiperidine compound (26) (50 mg, 0.17 mmol) obtained in the process 3 was used to cause the same reaction as process 2 of example 1, thus obtained example 15 compound (27:R=2,2-dimethylcyclopropane) in the form of a yellow-white crystal (14.9 mg, 22%).

1H-NMR (300 MHz, CDCl$_3$) δ=0.68–0.72 (1H, m), 0.81–0.85 (1H, m), 1.04–1.09 (1H, m), 1.09–1.23 (14H, m), 1.40–1.45 (1H, m), 1.49–1.58 (1H, m), 1.87–1.92 (2H, m), 2.10–2.19 (2H, m), 2.84 (2H, m), 3.51 (2H, s), 3.74–3.85 (1H, m), 5.50 (2H, d, J=8.4 Hz), 7.26 (2H, d, J=8.4 Hz), 7.48 (2H, d, J=8.4 Hz), 7.55 (1H, s). MS(ESI) m/z 398(M+H)$^+$.

EXAMPLE 16

Process 1:

An acetonitrile (5 ml) solution of the piperidine compound (23:R=2,2-dimethylcyclopropane) (50 mg, 0.25 mmol) obtained in the process 1 of example 15 was added with 2-(4-t-butoxycarbonylaminophenyl)ethanol paratoluensulfonate (57 mg, 0.31 mmol), sodium carbonate (32 mg, 0.31 mmol) and sodium iodide (2 mg), which was in turn heated and refluxed at 100° C. for 2 hours. The resultant was extracted with ethyl acetate, and further washed with water and saturated saline solution, dried and vacuum concentrated, and then separately purified with a silica gel TLC plate (chloroform, methanol), thus obtained a phenethylpiperidine compound (31 mg, 29%).

1H-NMR (300 MHz, CDCl$_3$) δ=0.69–0.74 (1H, m), 1.08 (1H, t, J=4.8 Hz), 1.13 (3H, s), 1.66 (3H, s), 1.20–1.26 (2H, m), 1.50–1.64 (2H, m), 1.51 (9H, s), 1.95 (2H, brs), 2.17–2.20 (2H, m), 2.57–2.62 (2H, m), 2.74–2.79 (2H, m), 2.94–2.99 (2H, m), 3.77–3.88 (1H, m), 5.45–5.48 (1H, m), 6.45 (1H, s), 7.10 (2H, d, J=8.4 Hz), 7.23–7.28 (2H, m).

Process 2:

4M hydrochloric acid-dioxane solution was dropped by 1 ml into a dichloromethane (3 ml) solution of the phenethylpiperidine (30.9 mg, 0.074 mmol) obtained in the process 1, which was in turn stirred at the room temperature for 3 hours. Further, 4M hydrochloric acid-dioxane solution was added by another 1 ml to the solution, which was then stirred again at the room temperature for 1 hour. After the solvent was distilled out, the resultant was extracted with ethyl acetate, and washed with saturated aqueous solution of sodium hydrogen carbonate, water and saturated saline solution, dried and then vacuum concentrated, thus obtained a deprotected compound in the form of a light yellow crystal (9.7 mg, 41%).

1H-NMR (300 MHz, CDCl$_3$) δ=0.69–0.74 (1H, m), 1.08 (1H, t, J=4.8 Hz), 1.14 (3H, s), 1.67 (3H, s), 1.20–1.26 (2H, m), 1.50–1.64 (2H, m), 1.95 (2H, brs), 2.19–2.25 (2H, m), 2.57–2.62 (2H, m), 2.70–2.76 (2H, m), 2.98–3.02 (2H, m), 3.58 (2H, brs), 3.58–3.78 (1H, m), 5.45–5.48 (1H, m), 6.62 (2H, d, J=8.4 Hz), 6.98 (2H, d, J=8.4 Hz).

MS(ESI) m/z 316 (+H)$^+$.

Process 3:

The deprotected compound obtained in the process 2 was used as a starting material, which experienced the same reaction as the process 2 of example 1, and a compound of example 16 was obtained in the form of a yellow-white crystal (3.8 mg, 31%).

1H-NMR (300 MHz, CDCl$_3$) δ=0.69–0.74 (1H, m), 0.81–0.86 (1H, m), 1.08 (1H, t, J=4.8 Hz), 1.13–1.26 (14H, m), 1.37–1.41 (1H, m), 1.54–1.64 (2H, m), 1.94–2.00 (2H, m), 2.20–2.29 (2H, m), 2.61–2.67 (2H, m), 2.78–2.84 (2H, m), 3.01–3.05 (2H, m), 3.81–3.88 (1H, m), 5.47 (1H, d, J=8.7 Hz), 7.13 (2H, d, J=8.4 Hz), 7.14 (1H, s), 7.43 (2H, d, J=8.4 Hz). MS(ESI) m/z 412(M+H)$^+$.

EXAMPLE 17

According to the same method as of example 1, a compound of example 17 was synthesized by using 3-nitrophenol and 2-chloro-5-nitropyridine as a starting material.

1H-NMR (300 MHz, DMSO-d6) δ=0.74–0.84 (2H, m), 0.94–1.02 (2H, m), 1.12 (3H, s), 1.15 (6H, s), 1.17 (3H, s), 1.60–1.67 (2H, m), 6.70–6.76 (1H, m), 6.99 (1H, d, J=8.7 Hz), 7.24–7.44 (3H, m), 8.08 (1H, dd, J=8.7, 2.7 Hz), 8.35 (1H, d, J=2.7 Hz), 10.14 (1H, brs), 10.25 (1H, brs). MS(ESI) m/z 394(M+H)$^+$.

EXAMPLE 18

According to the same method as of example 1, a compound of example 18 was synthesized by using 2-nitrophenol and 2-chloro-5-nitropyridine as a starting material.

1H-NMR (300 MHz, DMSO-d6) δ=0.82–0.87 (2H, m), 0.98–1.03 (2H, m), 1.12–1.18 (14H, m), 1.64–1.70 (2H, m), 6.96–7.17 (3H, m), 7.43 (1H, d, J=8.4 Hz), 8.08 (1H, dd, J=8.4, 3.0 Hz), 8.27–8.31 (1H, m), 8.59 (1H, d, J=3.0 Hz), 9.42 (1H, s), 10.22 (1H, s).

MS(ESI) m/z 394(M+H)$^+$.

EXAMPLE 19

According to the same method as of example 12, a compound of example 19 was synthesized by using 2-hydroxy-5-nitropyridine and 3-nitrobenzylbromide as a starting material.

1H-NMR (300 MHz, DMSO-d6) δ=0.74–0.80 (2H, m), 0.90–1.02 (2H, m), 1.10–1.28 (12H, s), 1.52–1.57 (1H, m), 1.61–1.68 (1H, m), 4.96–5.13 (2H, m), 6.46 (1H, d, J=9.3 Hz), 6.90 (1H, d, J=8.1 Hz), 7.24 (1H, t, J=8.1 Hz), 7.40 (1H, s), 7.44 (1H, dd, J=9.3, 3.0 Hz), 7.60 (1H, d, J=8.1 Hz), 8.13 (1H, d, J=3.0 Hz), 9.83 (1H, s), 10.08 (1H, s). MS(ESI) m/z 408(M+H)$^+$.

EXAMPLE 20

According to the same method as of example 12, a compound of example 20 was synthesized by using 2-hydroxy-5-nitropyridine and 2-nitrobenzylbromide as a starting material.

1H-NMR (300 MHz, DMSO-d6) δ=0.75–0.85 (2H, m), 0.92–1.00 (2H, m), 1.10–1.20 (12H, s), 1.68–1.72 (2H, m), 5.02–5.20 (1H, m), 6.55 (1H, d, J=9.6 Hz), 7.08 (1H, d, J=7.5 Hz), 7.22–7.32 (1H, m), 7.50 (1H, dd, J=9.6, 3.0 Hz), 7.77–7.86 (1H, m), 8.08 (1H, d, J=7.5 Hz), 8.29 (1H, d, J=3.0 Hz), 10.02 (1H, s), 10.39 (1H, s). MS(ESI) m/z 408(M+H)$^+$.

EXAMPLE 21

According to example 8, a compound of example 21 was synthesized by using 3-amino-6-chloropyridazine and 3-nitrophenol as a starting material.

1H-NMR (300 MHz, DMSO-d6) δ=0.78 (1H, dd, J-7.8 Hz, 3.9 Hz), 0.85 (1H, dd, J=7.5 Hz, 3.9 Hz), 0.96 (1H, dd, J=6.0 Hz, 4.5 Hz), 1.02 (1H, dd, J=5.4 Hz, 4.2 Hz), 1.11–1.20 (12H, s), 1.64(1H, dd, J=7.8 Hz, 5.4 Hz), 1.92 (1H, dd, J=7.8 Hz, 5.7 Hz), 6.81 (1H, ddd, J=7.8 Hz, 2.3 Hz, 1.5 Hz), 7.32 (1H, t, J=8.0 Hz), 7.31 (1H, m), 7.44 (1H, d, J=9.6 Hz), 7.51 (1H, m), 8.37 (1H, d, J=9.3 Hz), 10.20 (1H, s), 11.16 (1H, s).

MS(ESI) m/z 395(M+H)$^+$.

EXAMPLE 22

According to the same method as of example 1, a compound of example 22 was synthesized by using 2-chloro-5-nitropyridine and 3-methyl-4-nitrophenol as a starting material.

1H-NMR (300 MHz, DMSO-d6) δ=0.75–0.81 (2H, m), 0.97 (2H, q, J=6.0, 10.2 Hz), 1.16 (12H), 1.65 (1H, t, J=8.1 Hz), 1.73 (1H, t, J=8.1 Hz), 2.17 (3H, s), 6.85 (1H, d, J=9.0 Hz), 6.92–6.97 (2H), 7.30 (1H, d, J=8.4 Hz), 8.06 (1H, dd, J=2.7, 9.0 Hz), 8.3 (1H, d, J=2.7 Hz), 9.41 (1H, s), 10.2 (1H, s). MS(ESI) m/z 408(M+H)$^+$, 406(M−H)$^-$.

EXAMPLE 23

According to the same method as of example 1, a compound of example 23 was synthesized by using 2-chloro-4-methyl-5-nitropyridine and 4-nitrophenol as a starting material.

1H-NMR (300 MHz, DMSO-d6) δ=0.75–0.81 (2H, m), 0.98–1.00 (2H, m), 1.14 (6H, s), 1.17 (6H, s), 1.59–1.73 (2H, m), 2.19 (3H, s), 6.85 (1H, s), 7.01 (2H, d, J=9.0 Hz), 7.60 (2H, d, J=9.0 Hz), 7.96 (1H, s). MS(ESI) m/z 408(M+H)$^+$, 406(M−H)$^-$.

EXAMPLE 24

According to the same method as of example 1, a compound of example 24 was synthesized by using 2-chloro-4-methyl-5-nitropyridine and 3-methyl-4-nitrophenol as a starting material.

1H-NMR (300 MHz, CDCl$_3$) δ=0.82–0.90 (2H, m), 1.15–1.30 (14H), 1.42–1.56 (2H, m), 2.28 (6H, s), 6.73 (1H, brs), 6.94 (2H, brs), 7.09 (2H, brs), 7.74 (1H, brs), 8.19 (1H, brs). MS(ESI) m/z 422(M+H)$^+$, 420(M−H)$^-$.

EXAMPLE 25

According to the same method as that used in the process 2 of example 1, a compound of example 25 was synthesized by using 6-(5-amino-2-pyridylthio)-3-pyridylamine as a starting material.

1H-NMR (300 MHz, DMSO-d6) δ=0.78–0.85 (2H, m), 0.97–1.05 (2H, m), 1.14 (6H, m), 1.16 (6H, s), 1.64–1.69 (2H, m), 7.2 (2H, d, J=8.7 Hz), 8.00 (2H, dd, J=8.72, 2.7 Hz), 8.67 (2H, d, J=2.7 Hz), 10.37 (2H, s). MS(ESI) m/z 411(M+H)$^+$.

EXAMPLE 26

According to the same method as that used in the process 2 of example 1, a compound of example 26 was synthesized by using 2,2-dichloro-cyclopropanecarbonylchloride as a starting material.

1H-NMR (300 MHz, DMSO-d6) δ=2.02 (2H, d, J=9.0 Hz), 2.50 (2H, s), 2.87 (2H, t, J=9.0 Hz), 7.01 (1H, d, J=8.7 Hz), 7.09 (2H, d, J=8.7 Hz), 7.62 (2H, d, J=8.7 Hz), 8.09 (1H, dd, J=3.0, 8.7 Hz), 8.35 (1H, d, J=3.0 Hz), 10.6 (1H, s), 10.8 (1H, s). MS(ESI) m/z 476(M+H)$^+$.

EXAMPLE 27

According to the same method as that used in the process 2 of example 1, a compound of example 27 was synthesized by using 2-methyl-cyclopropanecarbonylchloride as a starting material.

1H-NMR (300 MHz, DMSO-d6) δ=0.58–0.66 (2H, m), 0.76–1.00 (2H, m), 1.07 (3H, s), 1.08 (3H, s), 1.16–1.22 (2H, m), 1.45–1.49 (2H, m), 6.91 (1H, d, J=8.7 Hz), 6.98 (2H, d, J=9.0 Hz), 7.54 (2H, d, J=8.7 Hz), 7.99 (1H, dd, J=2.7, 9.0 Hz), 8.26 (1H, d, J=2.7 Hz), 8.26 (1H, d, J=2.7 Hz), 10.1 (1H, s), 10.2 (1H, s). MS(ESI) m/z 366(M+H)$^+$, 364(M−H)$^-$.

EXAMPLE 28

According to the same method as that used in the process 2 of example 1, a compound of example 28 was synthesized by using cyclohexane-carbonylchloride as a starting material.

1H-NMR (300 MHz, DMSO-d6) δ=1.17–1.14 (10H, m), 1.66–1.82 (10H, m), 2.31 (2H, br), 6.93 (1H, d, J=8.7 Hz), 6.99 (2H, d, J=8.7 Hz), 7.59 (2H, d, J=8.7 Hz), 8.04 (1H, dd, J=3.0, 8.7 Hz), 8.30 (1H, d, J=3.0 Hz), 9.80 (1H, s), 9.93 (1H, s). MS(ESI) m/z 422(M+H)$^+$.

EXAMPLE 29

According to the same method as that used in the process 2 of example 1, a compound of example 29 was synthesized by using 2-methyl-cyclohexanecarbonylchloride as a starting material.

1H-NMR (300 MHz, DMSO-d6) δ=0.82–0.90 (6H, m), 1.29–1.51 (12H, m), 1.64–1.69 (4H, m), 2.12 (2H, brs), 2.49–2.53 (2H, m), 6.93 (1H, d, J=8.7 Hz), 6.99 (2H, d, J=8.7 Hz), 7.59 (2H, d, J=8.7 Hz), 8.04 (1H, dd, J=3.0, 8.7 Hz), 8.30 (1H, d, J=3.0 Hz), 9.74 (1H, s), 9.86 (1H, s). MS(ESI) m/z 450 (M+H)$^+$.

EXAMPLE 30

According to the same method as that used in the process 2 of example 1, a compound of example 30 was synthesized by using 3-cyclohexane-carbonylchloride as a starting material.

1H-NMR (300 MHz, DMSO-d6) δ=1.55–1.62 (2H, m), 1.90 (2H, d, J=12 Hz), 2.13 (8H, d, J=14 Hz), 2.49–2.55 (4H, m), 6.95 (1H, d, J=8.7 Hz), 7.01 (2H, d, J=8.7 Hz), 7.61 (2H, d, J=8.7 Hz), 8.05 (1H, dd, J=3.0, 8.7 Hz), 8.33 (1H, d, J=3.0 Hz), 9.91 (1H, s), 10.0 (1H, s). MS(ESI) m/z 418(M+H)$^+$.

EXAMPLE 31

Process 1:

Sodium hydroxide (10 g) was dissolved into a mixed solution of water (100 ml) and dioxane (100 ml), which was added with 4-hydroxyaniline (10.9 g, 0.1 mol) under the ice water cooling and further added slowly with Boc$_2$O (27.3 g, 0.125 mmol), and then stirred at 0° C. for 4 hours. After the reaction having been completed, the solvent was evapolated, and the resultant was neutralized with aqueous solution of ammonium chloride, extracted with ethyl acetate, and after having been washed, dried and concentrated according to the conventional manner, then purified by way of the silica gel chromatography (ethyl acetate, hexane), thus obtained the objective 4-t-butoxycarbonylaminophenol (37) in the form of a white crystal (12.3 g, 58%).

1H-NMR (300 MHz, CDCl$_3$) δ=1.53 (9H, s), 5.30 (1H, brs), 6.35 (1H, brs), 6.73 (2H, d, J=8.7 Hz), 7.15 (2H, d, J=8.7 Hz).

Process 2:

The 4-t-butoxycarbonylaminophenol (37) (8.36 g, 40 mmol) obtained in the process 1, the 2-chloro-5-nitropyridine (36) (6.24, 40 mmol) and potassium carbonate (11.4 g, 80 mmol) were stirred in the dimethylformamide (100 ml) at 80° C. for 3 hours. After the reaction having been completed, the solvent was evaporated and the resultant was extracted with ethyl acetate, and after having been washed, dried and concentrated according to the conventional manner, then crystallized again with a mixed solvent of ethanol and ethyl acetate, thus obtained an objective ether compound (38) in the form of a yellow crystal (11.88 g, 90%).

1H-NMR (300 MHz, CDCl$_3$) δ=1.55 (9H, s), 6.54 (1H, brs), 7.01 (1H, d, J=8.5 Hz), 7.10 (2H, d, J=8.7 Hz), 7.45 (2H, d, J=8.7 Hz), 8.47 (1H, dd, J=8.5, 2.5 Hz), 9.04 (1H, d, J=2.5 Hz).

Process 3:

A mixed solvent of the ether compound (38) (2 g, 6.6 mmol) obtained in the process 2 mixed with ethanol (50 ml) and dioxane (20 ml) was added with 10%-palladium carbon (1 g) and reduced under the hydrogen pressure of 5 atmosphere at the room temperature for 15 hours. After the reaction having been completed, the solid matter was filtered out, and the filtrate was purified by way of the silica gel chromatography (ethyl acetate, hexane), thus obtained objective compound in the reduced form (39) (1.90 g, 93%).

1H-NMR (300 MHz, CDCl$_3$) δ=1.55 (9H, brs), 6.44 (1H, brs), 6.74 (1H, d, J=8.5 Hz), 7.01 (2H, d, J=8.7 Hz), 7.06 (1H, dd, J=8.5, 3.0 Hz), 7.34 (2H, d, J=8.7 Hz), 7.70 (1H, d, J=3.0 Hz).

Process 4:

A dichloromethane (100 ml) solution of the reduced form (39) (1.6 g, 5.3 mmol) obtained in the process 3 and triethylamine (2 g, 20 mmol) was added with dichloromethane (10 ml) solution of 2,2-dimethylcyclopropanecarbonylchloride (1.05 mg, 8 mmol), which was in turn stirred at the room temperature for 4 hours. After the reaction having been completed, the solvent was distilled out under reduced-pressure condition and the resultant was extracted with ethyl acetate, and after having been washed, dried and concentrated according to the conventional manner, then the resultant was purified by way of the silica gel chromatography (ethyl acetate, hexane), thus obtained an objective amide compound (40:R2=2,2-dimethylcyclopropane) in the form of a white crystal (1.95 g, 67%).

1H-NMR (300 MHz, DMSO-d6) δ=0.76–0.83 (1H, m), 0.95–1.02 (1H, m), 1.17 (3H, s), 1.19 (3H, s), 1.55 (9H, brs), 1.60–1.66 (1H, m), 6.92 (1H, d, J=9.1 Hz), 6.99 (2H, d, J=8.7 Hz), 7.44 (2H, d, J=8.7 Hz), 8.03 (1H, dd, J=9.1, 3.8 Hz), 8.30 (1H, d, J=3.8 Hz), 9.33 (1H, s), 10.20 (1H, s).

Process 5:

An ethanol (50 ml) solution of the amide compound (40:R2=2,2-dimethylcyclopropane) (8 g, 20 mmol) obtained in the process 4 was added with 4M hydrochloric acid-dioxane solution (20 ml) and stirred at the room temperature for 20 hours. After the reaction having been completed, the solvent was distilled out under reduced-pressure condition, and then dimethyl ether (50 ml) was added into the resultant to be crystallized, thus obtained an objective hydrochloride of the amine body (41:R2=2,2-dimethylcyclopropane) in the form of a brown crystal (7.24 g, yield of 98% as 2hydrochloride).

1H-NMR (300 MHz, DMSO-d6) δ=0.78 (1H, dd, J=7.8, 3.9 Hz), 0.94–0.98 (1H, m), 1.12 (3H, s), 1.14 (3H, s), 1.66 (1H, dd, J=7.8, 5.1 Hz), 7.03 (1H, d, J=9.0 Hz), 7.18 (2H, d, J=8.7 Hz), 7.40 (2H, d, J=8.7 Hz), 8.09 (1H, dd, J=8.7, 2.7 Hz), 8.34 (1H, d, J=2.7 Hz), 10.00–10.06 (2H, br), 10.36 (1H, s).

Process 6:

A methylene chloride solution (10 ml) of the hydrochloride (111 mg, 0.33 mmol) of the amine compound (41:R2=2,2-dimethylcyclopropane) obtained in the process 5 was added with triethylamine (202 mg, 2.0 mmol) and cooled in the ice bath, into which the methylene chloride solution (5 ml) of benzoylchloride (72 mg, 0.51 mmol) was dropped. After the reaction was completed, the resultant was concentrated, extracted with methylene chloride, and after having been washed, dried and concentrated according to the conventional manner, then purified by way of the silica gel column chromatography (methylene chloride, methanol), thus obtained a compound of example 31 (117 mg).

H-NMR (300 MHz, DMSO-d6) δ=0.79–0.83 (1H, m), 0.99 (1H, t, J=4.5 Hz), 1.16 (6H, d, J=6.5 Hz), 1.66 (1H, t, 6.5 Hz), 6.97 (1H, d, J=9.2 Hz), 7.08 (2H, dd, J=2.1, 6.5 Hz), 7.51–7.60 (3H, m), 7.77 (2H, dd, J-2.1, 6.5 Hz), 8.07 (1H, dd, J=2.7, 9.2 Hz), 8.32 (1H, d, J=2.7 Hz), 10.2 (1H, s), 10.4 (1H, s). MS(ESI) m/z 402(M+H)$^+$.

EXAMPLE 32

According to the same method as of the process 6 of example 31, a compound of example 32 was synthesized by using phenyl-acetylchloride and the hydrochloride of the amine compound (41) obtained in the process 5 of example 31 as a starting material.

1H-NMR (300 MHz, DMSO-d6) δ=0.79–0.83 (1H, m), 0.99 (1H, t, J=4.5 Hz), 1.16 (6H, d, J=6.5 Hz), 1.66 (1H, t,

J=6.5 Hz), 3.62 (1H, s), 6.91 (1H, d, J=9.2 Hz), 7.02 (2H, d, J=6.5 Hz), 7.21–7.37 (5H, m), 7.59 (2H, d, 6.5 Hz), 8.04 (1H, dd, J=2.7, 9.2 Hz), 8.30 (1H, d, J=2.7 Hz), 10.2 (2H, d, 6.0 Hz). MS(ESI) m/z 416(M+H)$^+$.

EXAMPLE 33

According to the same method as of the process 6 of example 31, a compound of example 33 was synthesized by using 4-chlorophenylacetylchloride and the hydrochloride of the amine body (41) obtained in the process 5 of example 31 as a starting material.

1H-NMR (300 MHz, DMSO-d6) δ=0.76–0.83 (1H, m), 0.95–1.02 (1H, m), 1.17 (3H, s), 1.19 (3H, s), 1.60–1.66 (1H, m), 3.65 (2H, s), 6.94 (1H, d, J=9.1 Hz), 7.03 (2H, d, J=8.7 Hz), 7.34–7.42 (4H, m), 7.59 (2H, d, J=8.7 Hz), 8.05 (1H, dd, J=9.1, 3.8 Hz), 8.30 (1H, d, J=3.8 Hz), 10.20 (1H, s). MS(ESI) m/z 450(M+H)$^+$.

EXAMPLE 34

According to the same method as of the process 6 of example 31, a compound of example 34 was synthesized by using 4-methoxyphenyl-acetylchrolide and the hydrochloride (41) obtained in the process 5 of example 31 as a starting material.

1H-NMR (300 MHz, CDCl$_3$) δ=0.72–0.76 (1H, m), 1.17–1.22 (7H, m), 1.38–1.49 (1H, m), 3.69 (2H, s), 3.81 (3H, s), 6.79–6.90 (4H, m), 6.99 (2H, d, J=8.7 Hz), 7.26–7.33 (2H, m), 7.40 (2H, d, J=8.7 Hz), 7.64 (1H, s), 8.06 (1H, s). MS(ESI) m/z 446(M+H)$^+$.

EXAMPLE 35

According to the same method as of the process 6 of example 31, a compound of example 35 was synthesized by using 3,4-dimethoxy-pbenylacethylchrolide and the hydrochloride (41) obtained in the process 5 of example 31 as a starting material.

1H-NMR (300 MHz, DMSO-d6) δ=0.79–0.83 (1H, m), 0.989 (1H, t, J=4.5 Hz), 1.16 (6H, d, J=6.5 Hz), 1.66 (1H, t, 6.5 Hz), 3.55 (2H, s), 3.62 (3H, s), 3.77 (6H, s), 6.65 (2H, s), 6.93 (1H, d, J=9.2 Hz), 7.02 (2H, dd, J=2.1, 6.5 Hz), 7.60 (2H, d, J=6.5 Hz), 8.04 (1H, dd, J=2.7, 9.2 Hz), 8.30 (1H, d, J=2.7 Hz), 10.2 (1H, s), 10.4 (1H, s).

MS(ESI) m/z 506(M+H)$^+$.

EXAMPLE 36

According to the same method as of the process 6 of example 31, a compound of example 36 was synthesized by using 3,4,5-trimethoxy-phenylacethylchrolide and the hydrochloride (41) obtained in the process 5 of example 31 as a starting material.

1H-NMR (300 MHz, DMSO-d6) δ=0.79–0.83 (1H, m), 0.989 (1H, t, J=4.5 Hz), 1.16 (6H, d, J=6.5 Hz), 1.66 (1H, t, 6.5 Hz), 3.55 (2H, s), 3.71 (6H, d, J=6.0 Hz), 6.83–6.95 (5H, m), 7.02(2H, d, J=9.2 Hz), 7.59 (2H, d, J=9.2 Hz), 8.04 (1H, dd, J=2.7, 9.0 Hz), 8.30 (1H, d, J=2.7 Hz), 10.1 (1H, s), 10.2 (1H, s). MS(ESI) m/z 476(M+H)$^+$.

EXAMPLE 37

A methylene chloride solution (10 ml) of the hydrochloride (254 mg, 0.76 mmol) of the amine compound (41) obtained in the process 5 of example 31 was added with triethylamine by 0.15 ml and cooled in the ice bath, which was in turn further added with 4-phenylbutyric acid (144 mg, 0.88 mmol), WSC.HCl (173 mg, 0.90 mmol) and stirred over night. After the reaction having been completed, the resultant was concentrated and separately purified by way of the silica gel chromatography, thus obtained a compound (277 mg) of example 37.

1H-NMR (300 MHz, DMSO-d6) δ=0.79–0.83 (1H, m), 0.989 (1H, t, J=4.5 Hz), 1.16 (6H, d, J=6.5 Hz), 1.66 (1H, t, J=6.5 Hz), 1.86–1.95 (2H, m), 2.32 (2H, t, J=7.5 Hz), 2.63 (2H, t, J=7.5 Hz), 6.94 (1H, d, J=9.0 Hz), 7.01 (2H, dd, J=1.4 Hz), 7.17–7.24 (5H, m), 8.05 (1H, d, J=9.0 Hz), 8.30 (1H, s), 9.89 (1H, s), 10.2 (1H, s). MS(ES) m/z 444(M+H)$^+$.

EXAMPLE 38

A DMF solution (10 ml) of the hydrochloride (120 mg, 0.36 mmol) of the amine compound (41) obtained in the process 5 of example 31 was added with triethylamine (50 μl, 0.36 mmol), potassium carbonate (105 mg, 0.76 mmol), 2-buromoethylbenzene (58 μl, 0.43 mmol) and sodium iodide (89 mg, 0.59 mol) to cause a reaction at 90° C. After the reaction was completed, the resultant was extracted with methylene chloride, and then washed with a saturated saline solution, dried and concentrated, and then purified by way of the silica gel thin layer chromatography. A 4M-HCl ethyl acetate solution was applied to this resultant in an ether solvent, thus obtained a compound (13 mg) of example 38 as hydrochloride salt.

1H-NMR (300 MHz, DMSO-D6) δ=0.78–0.84 (1H, m), 0.94–1.00 (1H, m), 1.15 (3H, s), 1.18 (3H, s), 1.63–1.68 (1H, m), 2.90–3.00(4H, m), 7.02 (1H, d, J=9.2 Hz), 7.15 (2H, d, J=8.0 Hz), 7.29–7.32 (7H, m), 8.09 (1H, d, J=9.2 Hz), 8.36 (1H, d, J=2.8 Hz), 10.7 (1H, s). MS(ESI) m/z 402(M+H)$^+$, 400(M−H)$^−$.

EXAMPLE 39

According to the same method as of example 38, a compound of example 39 was synthesized by using 3-phenylpropylbromide and the hydrochloride of the amine compound (41) obtained in the process 5 of example 31 as a starting material.

1H-NMR (300 MHz, DMSO-d6) δ=0.78–0.84 (1H, m), 0.94–1.00 (1H, m), 1.14 (3H, s), 1.16 (3H, s), 1.63–1.68 (1H, m), 1.92–2.00 (2H, m), 2.68–2.71 (2H, m), 3.21–3.28 (2H, m), 7.04 (1H, d, J=8.7 Hz), 7.13–7.23 (5H, m), 7.29 (2H, d, J=7.0 Hz), 7.46 (2H, d, J=7.0 Hz), 8.10 (1H, d, J=2.8, 8~7 Hz), 8.35 (1H, d, J=2.8 Hz), 10.3 (1H, s).

MS(ESI) m/z 416(M+H)$^+$, 414(M−H)$^−$.

EXAMPLE 40

A dichloromethane solution (5 ml) of the hydrochloride (111 mg, 0.3 mmol) of the amine compound (41) obtained in the process 5 of example 31 was added with triethylamine (101 mg, 1 mmol) and phenylisocyanate (60 mg, 0.5 mmol) and stirred at the room temperature for 20 hours. The generated precipitate was filtered to be taken, thus obtained a compound of example 40 (23 mg, 18%) of a urea compound.

1H-NMR (300 MHz, DMSO-d6) δ=0.76–0.82 (1H, m), 0.97–1.00 (1H, m), 1.14 (3H, s), 1.16 (3H, s), 1.62–1.66 (1H, m), 6.92–7.05 (4H, m), 7.28 (2H, t, J=8.7 Hz), 7.45 (4H, d, J=8.7 Hz), 8.05 (1H, dd, J=9.0, 2.7 Hz), 8.30 (1H, d, J=2.4 Hz), 8.64 (1H, s), 8.66 (1H, s), 10.20 (1H, s). MS(ESI) m/z 415(M−H)$^−$.

EXAMPLE 41

A dichloromethane solution (5 ml) of the hydrochloride (111 mg, 0.3 mmol) of the amine compound (41) obtained in the process 5 of example 31 was added with triethylamine (101 mg, 1 mmol) and phenylisocyanate (68 mg, 0.5 mmol) and stirred at the room temperature for 20 hours. After the reaction was completed, the resultant was concentrated, extracted with methylene chloride, and after having been washed, dried and concentrated according to the conventional manner, further purified by way of the silica gel column chromatography (ethyl acetate, hexane), thus obtained a compound (83 mg, 64%) of example 41.

1H-NMR (300 MHz, DMSO-d6) δ=0.79–0.83 (1H, m), 0.97–1.00 (1H, m), 1.14 (3H, s), 1.17 (3H, s), 1.62–1.67 (1H, m), 6.98 (1H, d, J=8.7 Hz), 7.05 (2H, d, J=8.7 Hz), 7.13 (1H, t, J=7.5 Hz), 7.33 (2H, t, J=8.1 Hz), 7.45–7.51 (4H, m), 8.07 (1H, dd, J=8.7, 2.7 Hz), 8.32 (1H, d, J=2.7 Hz), 9.76 (2H, broad s), 10.22 (1H, s). MS(ESI) m/z 431(M−H)−.

EXAMPLE 42

A dichloromethane solution (5 ml) of the hydrochloride (111 mg, 0.3 mmol) of the amine compound (41) obtained in the process 5 of example 31 was added with triethylamine (202 mg, 2 mmol) and benzenesulfonylchloride (88 mg, 0.5 mmol) and stirred at the room temperature for 20 hours. After the reaction having been completed, the resultant was concentrated, extracted with methylene chloride, and after having been washed, dried and concentrated according to the conventional manner, further purified by way of the silica gel column chromatography (ethyl acetate, hexane), thus obtained a compound (43 mg, 33%) of example 42.

1H-NMR (300 MHz, DMSO-d6) δ=0.78–0.82 (1H, m), 0.96–1.00 (1H, m), 1.13 (3H, s), 1.16 (3H, s), 1.61–1.66 (1H, m), 6.90–6.97 (3H, m), 7.06 (2H, d, J=8.4 Hz), 7.50–7.65 (3H, m), 7.75 (2H, d, J=8.1 Hz), 8.04 (1H, dd, J=9.0, 2.7 Hz), 8.27 (1H, d, J=2.4 Hz), 10.20 (2H, s). MS(ESI) m/z 438(M+H)+.

EXAMPLE 43

According to the same method as of example 1, and by using (S)-2,2-dimethylcyclopropanecarbonylchloride in the process 2, a compound of example 43 was synthesized.

1H-NMR (300 MHz, DMSO-d6) δ=0.75–0.83 (2H, m), 0.96–1.01 (2H, m), 1.13–1.18 (12H, m), 1.60–1.68 (2H, m), 6.93 (1H, d, J=8.7 Hz), 7.00 (2H, d, J=8.7 Hz), 7,60 (2H, d, J=8.7 Hz), 8.05 (1H, dd, J=8.7, 2.7 Hz), 8.31 (1H, d, J=2.7 Hz), 10.07 (1H, s), 10.20 (1H, s). [α]D=+123.7° (c=0.3, MeOH).

EXAMPLE 44

According to the same method as of example 31, and by using (S)-2,2-dimethylcyclopropanecarbonylchloride in the process 4 and further using (R)-2,2-dimethylcyclopropanecarbonylchloride in the process 6, a compound of example 44 was synthesized.

1H-NMR (300 MHz, DMSO-d6) δ=0.75–0.82 (2H, m), 0.96–1.01 (2H, m), 1.13–1.18 (12H, m), 1.61–1.68 (2H, m), 6.93 (1H, d, J–8.7 Hz), 7.00 (2H, d, J=8.7 Hz), 7.60 (2H, d, J=8.7 Hz), 8.05 (1H, dd, J=8.7, 2.7 Hz), 8.31 (1H, d, J=2.7 Hz), 10.07 (1H, s), 10.21(1H, s).

EXAMPLE 45

According to the same method as of example 31, and by using (R)-2,2-dimethylcyclopropanecarbonylchloride in the process 4 and further using (R)-2,2-dimethylcyclopropanecarbonylchloride in the process 6, a compound of example 45 was synthesized.

1H-NMR (300 MHz, DMSO-d6) δ=0.75–0.82 (2H, m), 0.96–1.01 (2H, m), 1.13–1.18 (12H, m), 1.61–1.68 (2H, m), 6.93 (1H, d, J-8.7 Hz), 7.00 (2H, d, J=8.7 Hz), 7.60 (2H, d, J=8.7 Hz), 8.05 (1H, dd, J=8.7, 2.7 Hz), 8.30 (1H, d, J=2.7 Hz), 10.07 (1H, s), 10.20 (1H, s).

EXAMPLE 46

According to the same method as of example 1, and by using (R)-2,2-dimethylcyclopropanecarbonylchloride in the process 2, a compound of example 46 was synthesized.

1H-NMR (300 MHz, DMSO-d6) δ=0.75–0.82 (2H, m), 0.96–1.00 (2H, m), 1.13–1.18 (12H, m), 1.61–1.68 (2H, m), 6.92 (1H, d, J=8.7 Hz), 6.98 (2H, d, J=8.7 Hz), 7.58 (2H, d, J=8.7 Hz), 8.03 (1H, d, J=8.7, 2.7 Hz), 8.29 (1H, d, J=2.7 Hz), 10.06 (1H, s), 10.19 (1H, s). [α]D=−146.5° (c=0.17, MeOH). Those compounds synthesized in examples 1 to 46 are shown as follows:

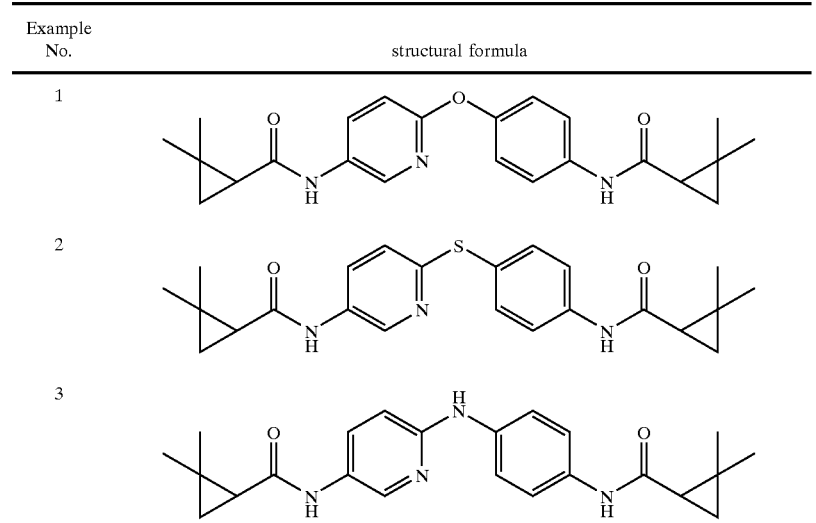

| Example No. | structural formula |
| --- | --- |
| 1 | |
| 2 | |
| 3 | |

-continued
| Example No. | structural formula |
|---|---|
| 4 | 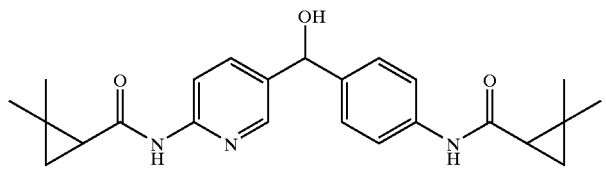 |
| 5 | 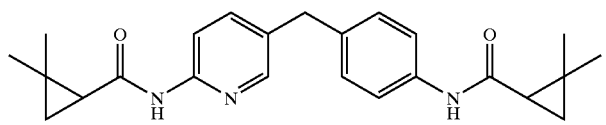 |
| 6 | 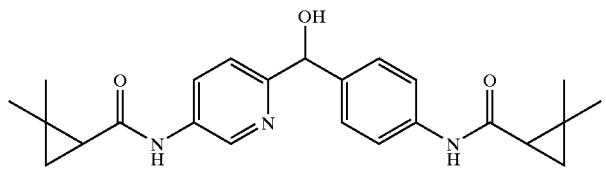 |
| 7 | 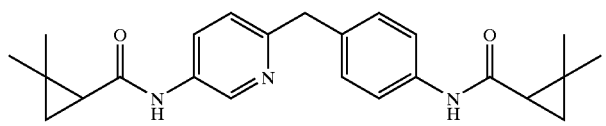 |
| 8 | 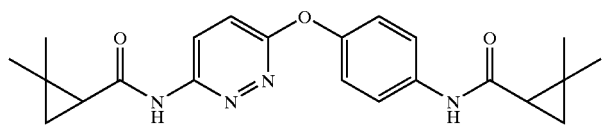 |
| 9 | 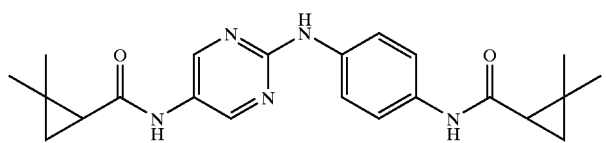 |
| 10 | 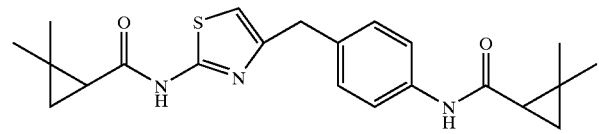 |
| 11 | 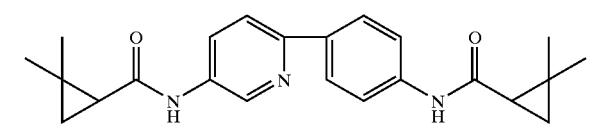 |
| 12 | 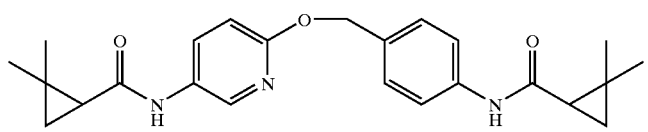 |
| 13 | 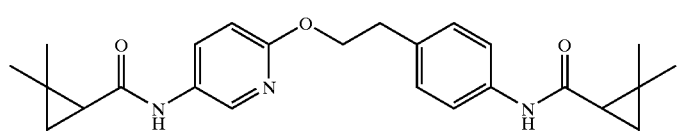 |

-continued
| Example No. | structural formula |
|---|---|
| 14 | 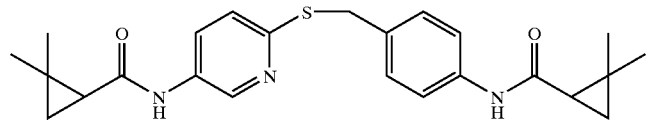 |
| 15 | 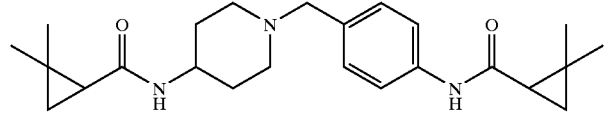 |
| 16 | 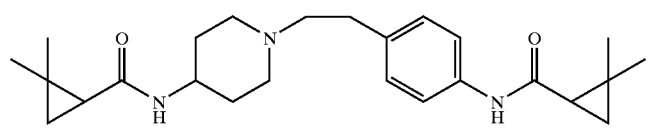 |
| 17 | 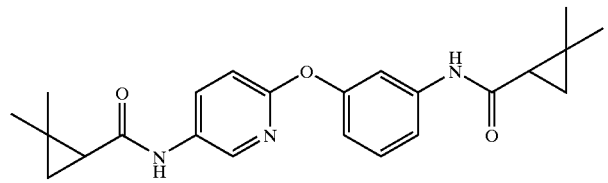 |
| 18 | 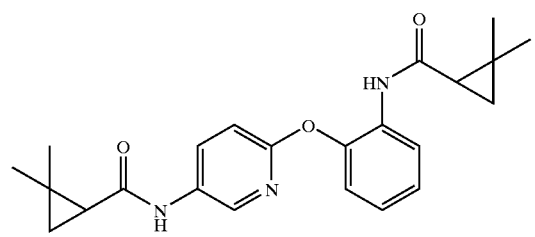 |
| 19 | 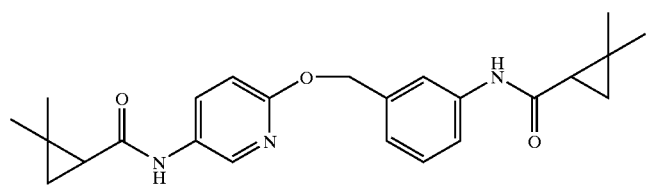 |
| 20 | 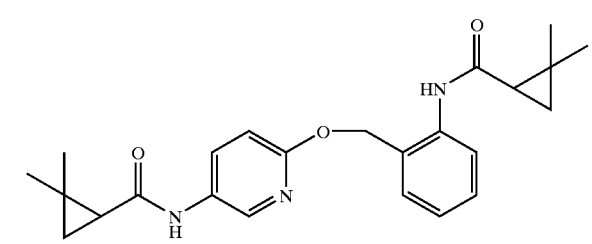 |
| 21 | 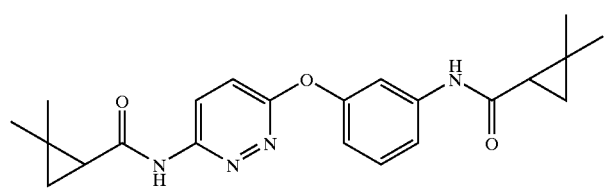 |

-continued
| Example No. | structural formula |
|---|---|
| 22 | 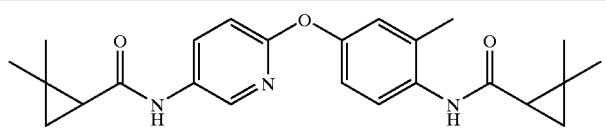 |
| 23 | 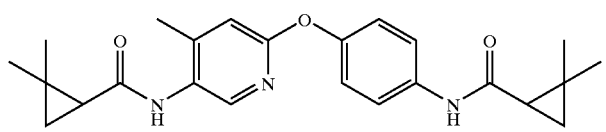 |
| 24 | 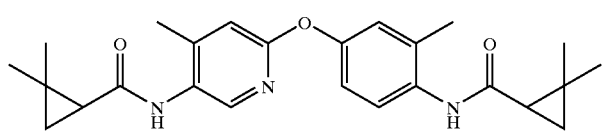 |
| 25 | 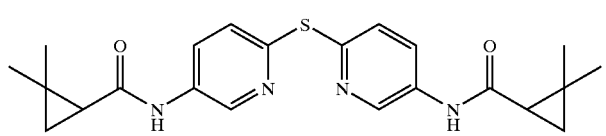 |
| 26 | 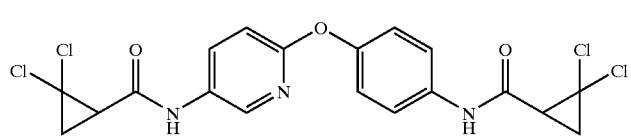 |
| 27 | 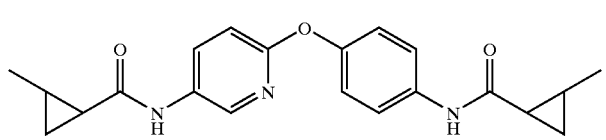 |
| 28 | 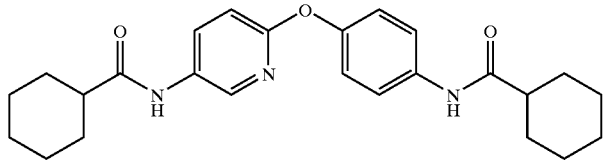 |
| 29 | 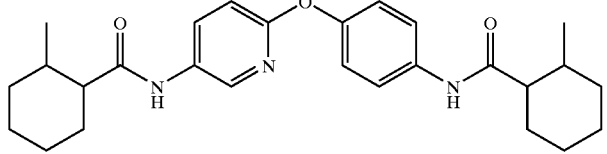 |
| 30 | 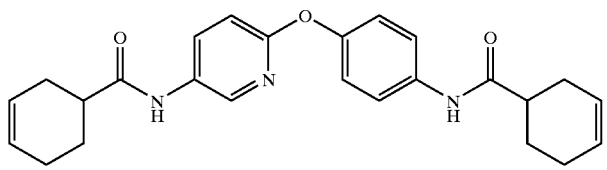 |
| 31 | 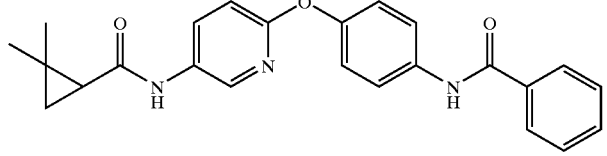 |

| Example No. | structural formula |
|---|---|
| 32 | 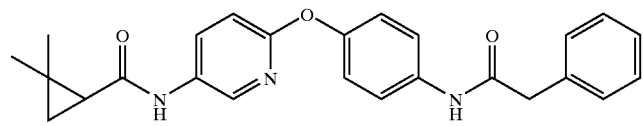 |
| 33 | 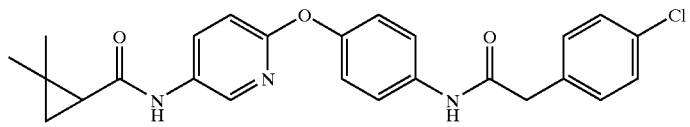 |
| 34 | 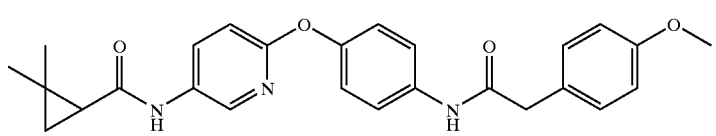 |
| 35 | 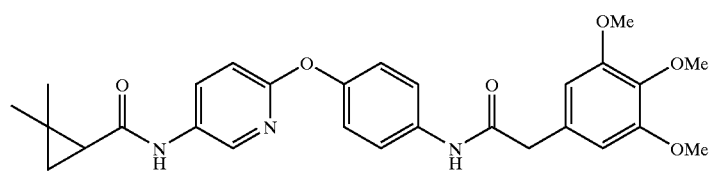 |
| 36 | 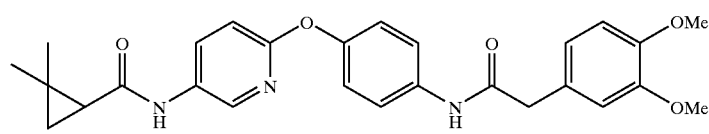 |
| 37 | 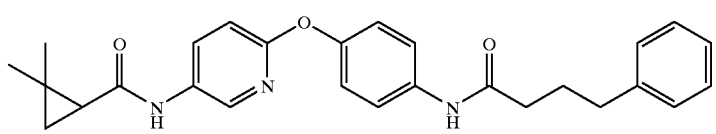 |
| 38 | 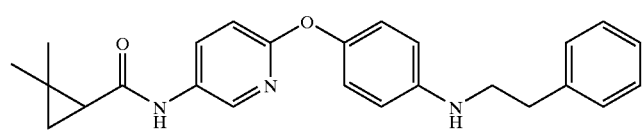 |
| 39 | 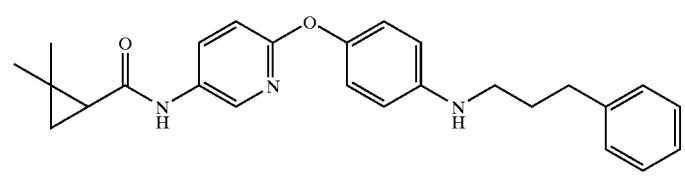 |
| 40 | 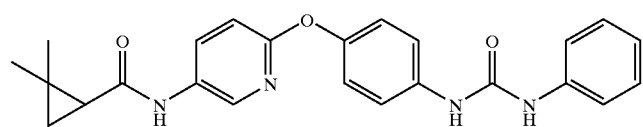 |
| 41 | 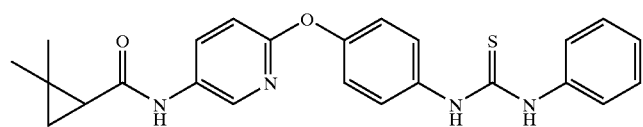 |

-continued

| Example No. | structural formula |
|---|---|
| 42 | (structure: tert-butyl-cyclopropyl-C(=O)-NH-pyridine-O-phenyl-NH-S(=O)$_2$-phenyl) |
| 43 | (structure: bis-amide with pyridine-O-phenyl linker, cyclopropyl groups) |
| 44 | (structure: bis-amide with pyridine-O-phenyl linker, cyclopropyl groups) |
| 45 | (structure: bis-amide with pyridine-O-phenyl linker, stereochemistry indicated) |
| 46 | (structure: bis-amide with pyridine-O-phenyl linker, stereochemistry indicated) |

EXAMPLE 47
Evaluation of the NF-kappa B Inhibition

Cells used for the tests were those prepared by stably introducing E. coli β-galactosidase (β-gal) genes driven by SV 40 minimum promoter fused with 6 tandems of the NF-KappaB binding motif derived from immunoglobulin kappa light chain enhancer into human normal umbilical cord vein endothelial cells (HUVEC) immortalized with SV 40 large T antigen. The cells were subcultured in RPMI medium containing 10% of FBS, and were seeded on a 96-well plate in a concentration of $1 \times 10^4$/well on a day before the start of the experiments. A compound of the present invention was dissolved in DMSO to obtain a solution of a proper concentration, which was added into the 96-well plate so that the final DMSO concentration would be not higher than 1%. 30 minutes after the addition of the compound, in order to induce NF-kappa B transcriptional activity, 1 ng/ml of IL-1 β was added to each well so as to obtain the final concentration of 50 ng/ml. β-gal activity was determined 16 hours after with a chemiluminescent substrate (Galacton-Light-Plus: Boehringer Mannheim) according to a protocol attached to the reagent. A Luminescence detector (ATTO) was used for the determination. In this evaluation system, β-gal activity induced by IL-1 β was substantially completely inhibited by glucocorticoid.

In the above evaluation, the compounds of the present invention exhibited the inhibiting effects.

The evaluation results for the compounds of the present invention are shown in Table 1.

TABLE 1

| Test compound | NFkB inhibition activity IC50 (μg/ml) |
|---|---|
| Example 1 | 0.5 |
| Example 2 | 0.3 |
| Example 3 | 0.8 |
| Example 4 | 1 |
| Example 5 | 0.9 |
| Example 6 | 0.4 |
| Example 7 | 1.5 |
| Example 8 | 1.5 |
| Example 9 | 0.7 |
| Example 14 | 0.015 |
| Example 22 | 0.15 |
| Example 26 | 0.15 |
| Example 29 | 1 |
| Example 31 | 1.5 |
| Example 32 | 0.1 |
| Example 33 | 0.2 |
| Example 34 | 0.3 |
| Example 37 | 0.09 |
| Example 38 | 0.05 |
| Example 39 | 0.035 |
| Example 43 | 0.25 |
| Example 44 | 0.1 |
| Example 45 | 1 |

EXAMPLE 48
Evaluation of AP-1 Inhibition

Cells used for the tests were those prepared by stably introducing E. coli β-galactosidase (β-gal) genes driven by SV 40 minimum promoter fused with 4 tandems of the AP-1 binding motif derived from human MMP-1 gene enhancer into human normal umbilical cord vein endothelial cells (HUVEC) immortalized with SV 40 large T antigen. The cells were subcultured in RPMI medium containing 10% of FBS, and were seeded on a 96-well plate in a concentration of $1\times10^4$/well on a day before the start of the experiments. A compound of the present invention was dissolved in DMSO to obtain a solution of a proper concentration, which was added into the 96-well plate so that the final DMSO concentration would be not higher than 1%. 30 minutes after the addition of the compound, phorbol-12-myristate-13-acetate (PMA) was added to each well so as to obtain the final concentration of 50 ng/ml. β-gal activity was determined 16 hours after with a chemiluminescent substrate (Galacton-Light-Plus: Boehringer Mannheim) according to a protocol attached to the reagent. A Luminescence detector (ATTO) was used for the determination. In this evaluation system, β-gal activity induced by PMA was substantially completely inhibited by glucocorticoid which is a known AP-1 inhibitor.

The compounds of the present invention exhibited the inhibition effect in these tests.

EXAMPLE 49

An antibody titer inhibition test and a delayed-type hypersensitivity reaction inhibition test Rhesus monkeys (female, aged four to six) subjected to the test were sensitized with 6Lf of TTx (Tetanus Toxoid) both in the back skin and in the femur muscle under anesthesia by an intramuscular injection of ketamine. The subject drug at the dose of 50 mg/kg had been administered twice daily (7:00 am and 7:00 pm) for 4 weeks starting at the day of TTx sensitization. The drug was suspended with 0.5% Tween 80 solution and was orally administered using a gastric catheter. The control animals were administered with the vehicle in the same manner as those for the test article. One ml of blood was drawn from femoral vein of each animal twice a week to obtain sera with which the anti-TTx antibody titer was evaluated by the ELISA method. The antibody titer was determined with OD of serially-diluted serum from 1:100 by 2 times and was defined as the degree of dilution reaching to "an average OD of the antibody before immunization+2×SD". One hour after the final administration in the morning on day 28, TTx was challenged once in the thoracic skin (10, 3, 1, 0.3, 0.1, 0.03 Lf/ml, 10 µl/site), and skin reactions at the injection sites were observed 24 and 48 hours after the TTx challenge. The delayed-type hypersensitivity reaction was scored according to the Draize dermal test criteria.

In the above evaluation, the compound of example 43 exhibited its inhibiting effect in both of the antibody titer and the delayed-type hypersensitivity reaction.

As is apparent from the result described above, the compounds of the present invention have an activity for inhibition the AP-1 or NF-KappaB activation, and thus are useful in providing the cure against the inflammatory diseases which might be involved in activation of those transcription factors. That is to say, the compounds of the present invention are useful as an anti-inflammatory agent, an anti-rheumatism agent, and immunosuppressive agent, a cancer metastasis inhibitor, and anti-viral agent or a therapeutic agent for arterial sclerosis, which can inhibit a number of gene expression, such as inflammatory cytokines, matrix metalloproteases, inflammatory cell adhesion molecules. Moreover, the compounds of the present invention are advantageously useful because they are free from side effects derived from hormonal action which has been observed in glucocorticoid.

What is claimed is:
1. A heterocyclic compound represented by formula (I) or a pharmaceutically acceptable salt thereof:

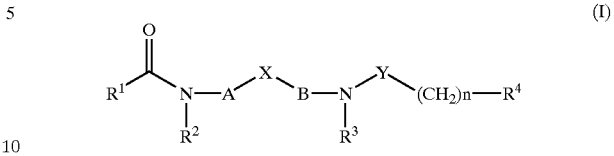

wherein $R^1$ is a cycloalkyl group, a cycloalkyl group having a substituent(s), wherein when said cycloalkyl group is a cyclopropyl group said cyclopropyl group has a substituent(s), a cycloalkenyl group or a cycloalkenyl group having a substituent(s); each $R^2$ and $R^3$ is a hydrogen atom or an alkyl group; $R^4$ is an alkyl group, an alkyl group having a substituent(s), an alkenyl group, an alkenyl group having a substituent(s), a cycloalkyl group, a cycloalkyl group having a substituent(s), a cycloalkenyl group, a cycloalkenyl group having a substituent(s), an aryl group, an aryl group having a substituent(s), an aromatic heterocyclic group having at least one hetero-atom within a ring or an aromatic heterocyclic group having a substituent(s) and at least one hetero-atom within a ring; A is a heterocyclic ring or a heterocyclic ring having a substituent(s); B is an aromatic ring, an aromatic ring having a substituent(s), a heterocyclic ring or a heterocyclic ring having a substituent(s); n is an integer selected from 0 to 6; —Y— is an interatomic bond, —CO—, —CO—O—, —CO—NR$^5$—, —CS—NR$^6$, —SO—, —SO$_2$—, wherein each of $R^5$ and $R^6$ respectively is a hydrogen atom or an alkyl group; wherein —X— is an interatomic bond, —O—, —O—CHR$^7$—, —CHR$^8$—O—, —O—CO—, —CO—O—, —O—CS—, —CS—O—, —S—, —SO—, —SO$_2$—, —S—CHR$^9$—, —CHR$^{10}$—S—, —S—CO—, —CO—S—, —S—CS—, —CS—S—, —SO$_2$—NR$^{11}$—, —NR$^{12}$—SO$_2$—, —NR$^{13}$—, —NR$^{14}$—CHR$^{15}$—, —CHR$^{16}$—NR$^{17}$—, —CO—, —C(=NOR$^{18}$)—, —C(=CHR$^{19}$)—, —CO—CHR$^{20}$—, —CHR$^{21}$—CO—, —CO—NR$^{22}$—, —NR$^{23}$—CO—, —CR$^{24}$R$^{25}$—, —CHR$^{26}$—CHR$^{27}$—, —CR$^{28}$=CR$^{29}$—, —O—CHR$^{30}$—CHR$^{31}$—, wherein each of $R^7$, $R^8$, $R^9$, $R^{10}$, $R^{15}$, $R^{16}$, $R^{20}$, $R^{21}$, $R^{24}$, $R^{28}$, $R^{29}$, $R^{30}$ and $R^{31}$ respectively is either of a hydrogen atom or an alkyl group; each of $R^{11}$, $R^{12}$, $R^{13}$, $R^{14}$, $R^{17}$, $R^{18}$, $R^{19}$, $R^{22}$ and $R^{23}$ respectively is either of a hydrogen atom, an alkyl group or an acyl group; each of $R^{26}$ and $R^{27}$ respectively is either of a hydrogen atom, a hydroxy group or an alkyl group; and $R^{25}$ is a hydrogen atom, a hydroxy group, an alkyl group, an alkyl group having a substituent(s), a mercapto group, an alkoxy group, an alkylthio group, an acyloxy group, an amino group, an alkylamino group, an amino group substituted with an amino protective group, a carboxyl group, an alkoxycarbonyl group, an aminocarbonyl group, or a cyano group.

2. The heterocyclic compound or pharmaceutically acceptable salt thereof according to claim 1, wherein $R^1$ of formula (I) is either of a 2,2-dimethylcyclopropyl group, a 2,2-dichlorocyclopropyl group, a 2,2-difluorocyclopropyl group or a 2,2-dibromocyclopropyl group.

3. The heterocyclic compound or pharmaceutically acceptable salt thereof according to claim 2, wherein, in formula (I), A is either of an aromatic heterocyclic ring or an aromatic heterocyclic ring having a substituent(s), and B is either of an aromatic ring, an aromatic ring having a substituent(s), an aromatic heterocyclic ring or an aromatic heterocyclic ring having a substituent(s).

4. The heterocyclic compound or pharmaceutically acceptable salt thereof according to claim 3, wherein —Y— of formula (I) is an interatomic bond, —CO—, —CONR$^5$—, CSNR$^6$— or —SO$_2$—, wherein each of R$^5$ and R$^6$ respectively is a hydrogen atom or an alkyl group.

5. The heterocyclic compound or pharmaceutically acceptable salt thereof according to claim 1, wherein, in formula (I), —X— is an interatomic bond, —O—, —O—CHR$^7$—, —CHR$^8$—O—, —S—, —NR$^{13}$—, —CR$^{24}$R$^{25}$— or —O—CHR$^{30}$—CHR$^{31}$—, wherein each of R$^7$, R$^8$, R$^{24}$, R$^{30}$ and R$^{31}$ respectively is a hydrogen atom or an alkyl group; R$^{13}$ is either of a hydrogen atom, an alkyl group or an acyl group; and R$^{25}$ is a hydrogen atom, a hydroxy group, an alkyl group, an alkyl group having a substituent(s), a mercapto group, an alkoxy group, an alkylthio group, an acyloxy group, an amino group, an alkylamino group, an amino group substituted with an amino protective group, a carboxyl group, an alkoxycarbonyl group, an aminocarbonyl group, or a cyano group.

6. The heterocyclic compound or pharmaceutically acceptable salt thereof according to claim 5, wherein, in formula (I), A is either of a pyridine, a pyridazine, a pyrimidine, a pyridine having a substituent(s), a pyridazine having a substituent(s) or a pyrimidine having a substituent (s); and B is a benzene ring or a benzene ring having a substituent(s).

7. The heterocyclic compound or pharmaceutically acceptable salt thereof according to claim 6, wherein R$^1$ and R$^4$ of formula (I) may be the same or different from each other and each may be either of a 2,2-dimethylcyclopropyl group, a 2,2-dichlorocyclopropyl group, a 2,2-difluorocyclopropyl group or a 2,2-diburomocyclopropyl group; —Y— is —CO—; and n is 0.

8. The heterocyclic compound or pharmaceutically acceptable salt thereof according to claim 6, wherein R$^1$ of formula (I) is either of a 2,2-dimethylcyclopropyl group, a 2,2-dichlorocyclopropyl group, a 2,2-difluorocyclopropyl group or a 2,2-dibromocyclopropyl group; R$^4$ is an aryl group or an aryl group having a substituent(s); —Y— is —CO—; and n is an integer selected from 1 to 3.

9. The heterocyclic compound or pharmaceutically acceptable salt thereof according to claim 6, wherein R$^1$ of formula (I) is either of a 2,2-dimethylcyclopropyl group, a 2,2-dichlorocyclopropyl group, a 2,2-difluorocyclopropyl group or a 2,2-dibromocyclopropyl group; R$^4$ is an aryl group or an aryl group having a substituent(s); —Y— is an interatomic bond; and n is an integer selected from 2 to 4.

10. The heterocyclic compound or pharmaceutically acceptable salt thereof according to claim 2, wherein when R$^1$ of formula (I) is a cyclopropyl group having a substituent(s), an absolute configuration of the carbon atom on the cyclopropyl group adjacent to the carbonyl group is S.

11. The heterocyclic compound or pharmaceutically acceptable salt thereof according to claim 2, wherein when R$^1$ of formula (I) is a cyclopropyl group having a substituent(s), an absolute configuration of the carbon atom on the cyclopropyl group adjacent to the carbonyl group is R.

12. The heterocyclic compound or pharmaceutically acceptable salt thereof according to claim 7, wherein when each of R$^1$ and R$^4$ of formula (I) is a cyclopropyl group having a substituent(s), an absolute configuration of the carbon atom on the cyclopropyl group adjacent to the carbonyl group is S.

13. The heterocyclic compound or pharmaceutically acceptable salt thereof according to claim 7, wherein each of R$^1$ and R$^4$ of formula (I) is a cyclopropyl group having a substituent(s), an absolute configuration of the carbon atom on the cyclopropyl group adjacent to the carbonyl group is R.

14. A heterocyclic compound or a pharmaceutically acceptable salt thereof represented by the following formulas:

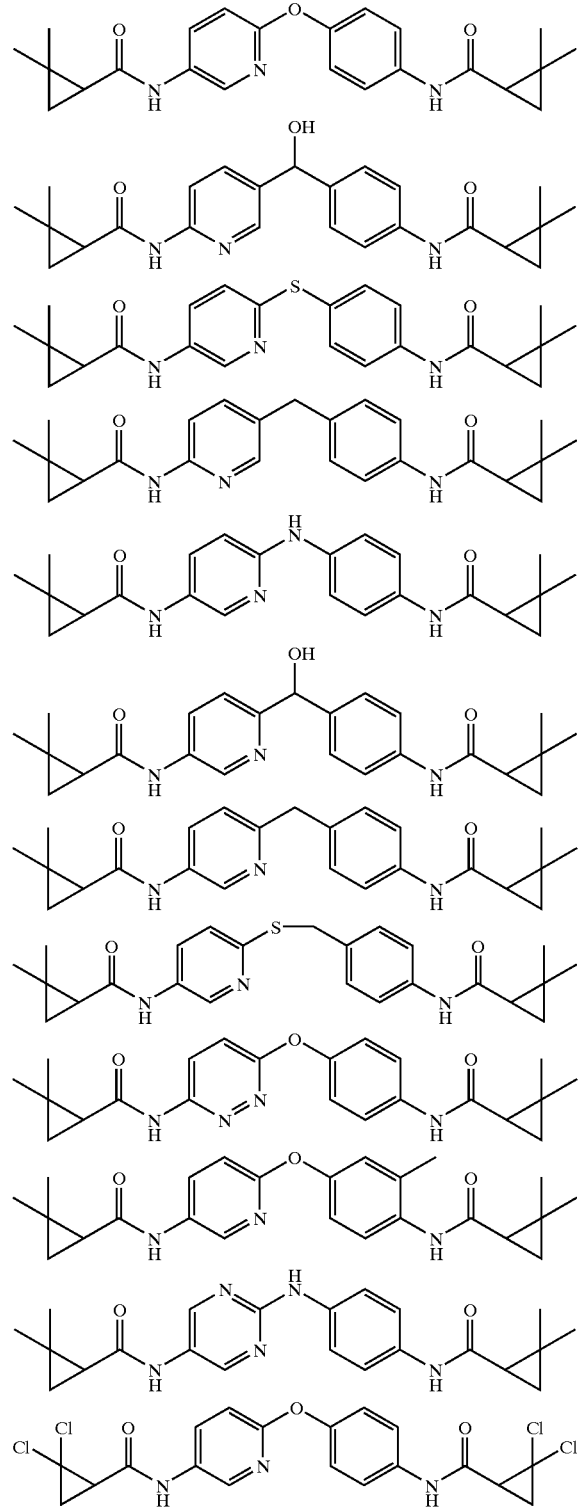

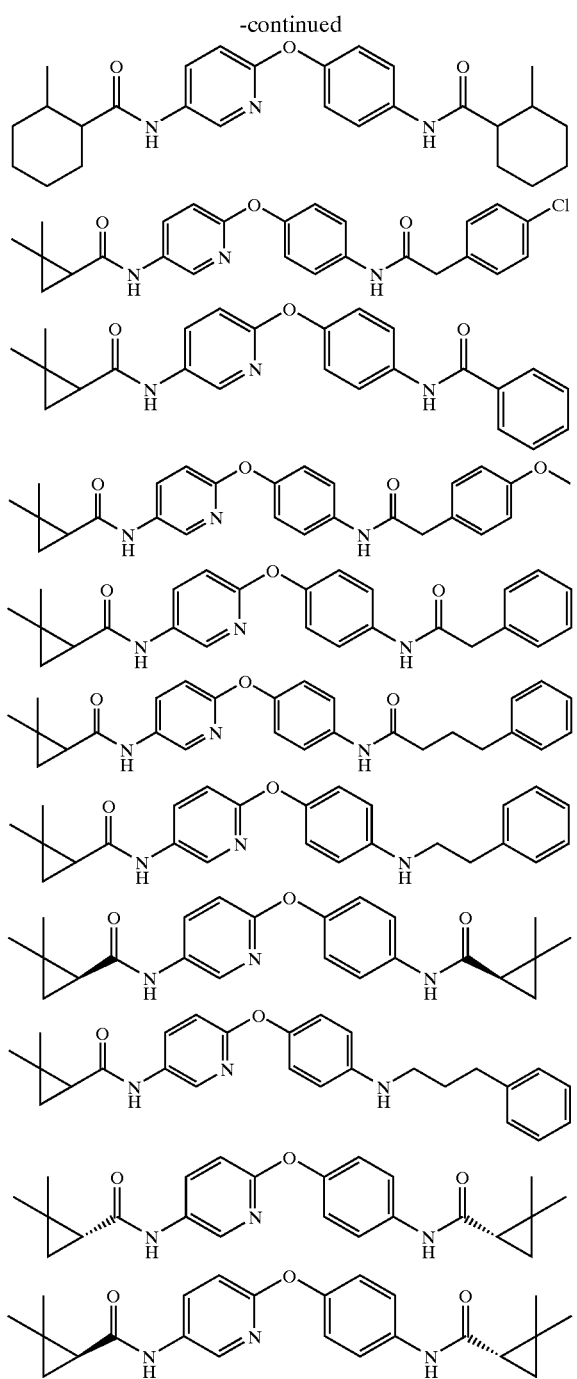

15. The heterocyclic compound or pharmaceutically acceptable salt thereof according to claim 1, wherein B is a phenylene group; $R^1$ is a cycloalkyl group having a substituent(s) or a cycloalkenyl group having a substituent(s); $R^2$ is a hydrogen atom or an alkyl group; $R^3$ is a hydrogen atom or an alkyl group; $R^4$ is an alkyl group which may be substituted, a cycloalkyl group which may be substituted, a cycloalkenyl group which may be substituted, an aryl group which may be substituted or an aromatic heterocyclic ring group which may be substituted and also has one or more hetero atoms; —X— is —O—, —O—$CHR^7$—, —$CHR^8$—O—, —O—CO—, —CO—O—, —O—CS—, —CS—O—, —S—, —SO—, —$SO_2$—, —S—$CHR^9$—, —$CHR^{10}$—S—, —S—CO—, —CO—S—, —S—CS—, —CS—S—, —$SO_2$—$NR^{11}$—, —$NR^{12}$—$SO_2$—, —$NR^{13}$—, —$NR^{14}$—$CHR^{15}$—, —$CHR^{16}$—$NR^{17}$—, —CO—, —C(=$NOR^{18}$)—, —C(=$CHR^{19}$)—, —CO—$CHR^{20}$—, —$CHR^{23}$—CO—, —CO—$NR^{22}$—, —$NR^{23}$—CO—, —$CR^{24}R^{25}$—, —$CHR^{26}$—$CHR^{27}$— or —$CR^{28}$=$CR^{29}$, wherein each of $R^7$, $R^8$, $R^{10}$, $R^{20}$, $R^{21}$, $R^{24}$, $R^{28}$ and $R^{29}$ is either of a hydrogen atom or an alkyl group; each of $R^{11}$, $R^{12}$, $R^{13}$, $R^{14}$, $R^{17}$, $R^{18}$, $R^{19}$, $R^{22}$ and $R^{23}$ is either of a hydrogen atom, an alkyl group or an acyl group; each of $R^{15}$ and $R^{16}$ is a hydrogen atom or an alkyl group; each of $R^{26}$ and $R^{27}$ is either of a hydrogen atom, a hydroxy group or an alkyl group; and $R^{25}$ is a hydrogen atom, a hydroxy group, an alkyl group which may be substituted, a mercapto group, an alkoxy group, an alkylthio group, an acyloxy group, an amino group which may be substituted with an alkyl group or an amino protective group, a carboxyl group, an alkoxycarbonyl group, an aminocarbonyl group, or a cyano group; wherein n is an integer selected from 0 to 6; Y is —C(O)—; and A is the aromatic heterocyclic ring including at least one or more nitrogen atom.

16. The heterocyclic compound or pharmaceutically acceptable salt thereof according to claim 3, wherein when $R^1$ of formula (I) is a cyclopropyl group having a substituent(s), an absolute configuration of the carbon atom on the cyclopropyl group adjacent to the carbonyl group is S.

17. The heterocyclic compound or pharmaceutically acceptable salt thereof according to claim 3, wherein when $R^1$ of formula (I) is a cyclopropyl group having a substituent(s), an absolute configuration of the carbon atom on the cyclopropyl group adjacent to the carbonyl group is R.

18. The heterocyclic compound or pharmaceutically acceptable salt thereof according to claim 4, wherein when $R^1$ of formula (I) is a cyclopropyl group having a substituent(s), an absolute configuration of the carbon atom on the cyclopropyl group adjacent to the carbonyl group is S.

19. The heterocyclic compound or pharmaceutically acceptable salt thereof according to claim 4, wherein when $R^1$ of formula (I) is a cyclopropyl group having a substituent(s), an absolute configuration of the carbon atom on the cyclopropyl group adjacent to the carbonyl group is R.

20. The heterocyclic compound or pharmaceutically acceptable salt thereof according to claim 5, wherein when $R^1$ of formula (I) is a cyclopropyl group having a substituent(s), an absolute configuration of the carbon atom on the cyclopropyl group adjacent to the carbonyl group is S.

21. The heterocyclic compound or pharmaceutically acceptable salt thereof according to claim 5, wherein when $R^1$ of formula (I) is a cyclopropyl group having a substituent(s), an absolute configuration of the carbon atom on the cyclopropyl group adjacent to the carbonyl group is R.

22. The heterocyclic compound or pharmaceutically acceptable salt thereof according to claim 6, wherein when $R^1$ of formula (I) is a cyclopropyl group having a substituent(s), an absolute configuration of the carbon atom on the cyclopropyl group adjacent to the carbonyl group is S.

23. The heterocyclic compound or pharmaceutically acceptable salt thereof according to claim 6, wherein when $R^1$ of formula (I) is a cyclopropyl group having a substituent(s), an absolute configuration of the carbon atom on the cyclopropyl group adjacent to the carbonyl group is R.

24. The heterocyclic compound or pharmaceutically acceptable salt thereof according to claim 7, wherein when $R^1$ of formula (I) is a cyclopropyl group having a substituent(s), an absolute configuration of the carbon atom on the cyclopropyl group adjacent to the carbonyl group is S.

25. The heterocyclic compound or pharmaceutically acceptable salt thereof according to claim 7, wherein when $R^1$ of formula (I) is a cyclopropyl group having a substituent(s), an absolute configuration of the carbon atom on the cyclopropyl group adjacent to the carbonyl group is R.

26. The heterocyclic compound or pharmaceutically acceptable salt thereof according to claim 8, wherein when $R^1$ of formula (I) is a cyclopropyl group having a substituent(s), an absolute configuration of the carbon atom on the cyclopropyl group adjacent to the carbonyl group is S.

27. The heterocyclic compound or pharmaceutically acceptable salt thereof according to claim 8, wherein when $R^1$ of formula (I) is a cyclopropyl group having a substituent(s), an absolute configuration of the carbon atom on the cyclopropyl group adjacent to the carbonyl group is R.

28. The heterocyclic compound or pharmaceutically acceptable salt thereof according to claim 9, wherein when $R^1$ of formula (I) is a cyclopropyl group having a substituent(s), an absolute configuration of the carbon atom on the cyclopropyl group adjacent to the carbonyl group is S.

29. The heterocyclic compound or pharmaceutically acceptable salt thereof according to claim 9, wherein when $R^1$ of formula (I) is a cyclopropyl group having a substituent(s), an absolute configuration of the carbon atom on the cyclopropyl group adjacent to the carbonyl group is R.

30. A pharmaceutical composition comprising as an active ingredient which is a heterocyclic compound or a pharmaceutically acceptable salt thereof according to claim 1 and a pharmaceutical acceptable carrier.

31. A method of AP-1 activation inhibition or NF-kappaB activation inhibition comprising administering a pharmaceutical composition comprising as an active ingredient which is a heterocyclic compound or a pharmaceutically acceptable salt thereof according to claim 1.

32. A method of inflammatory cytokine production inhibition, production inhibition for matrix metalloprotease or inflammatory cell adhesion factor expression inhibition comprising administering a pharmaceutical composition comprising as an active ingredient which is a heterocyclic compound or a pharmaceutically acceptable salt thereof according to claim 1.

* * * * *